US011802882B2

(12) United States Patent
Gibbons et al.

(10) Patent No.: US 11,802,882 B2
(45) Date of Patent: *Oct. 31, 2023

(54) METHODS FOR THE DETECTION OF ANALYTES IN SMALL-VOLUME BLOOD SAMPLES

(71) Applicant: Labrador Diagnostics LLC, Wilmington, DE (US)

(72) Inventors: Ian Gibbons, Newark, CA (US); Shaunak Roy, Palo Alto, CA (US); Edmond Ku, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 1200 days.

This patent is subject to a terminal disclaimer.

(21) Appl. No.: 16/222,845

(22) Filed: Dec. 17, 2018

(65) Prior Publication Data

US 2019/0128902 A1    May 2, 2019

Related U.S. Application Data

(60) Continuation of application No. 15/054,510, filed on Feb. 26, 2016, now Pat. No. 10,156,579, which is a continuation of application No. 14/285,562, filed on May 22, 2014, now Pat. No. 9,303,286, which is a division of application No. 12/750,518, filed on Mar. 30, 2010, now Pat. No. 8,778,665, which is a continuation of application No. 11/939,509, filed on Nov. 13, 2007, now abandoned.

(60) Provisional application No. 60/865,805, filed on Nov. 14, 2006.

(51) Int. Cl.
| | | |
|---|---|---|
| *G01N 33/92* | (2006.01) | |
| *B01L 3/00* | (2006.01) | |
| *G01N 21/31* | (2006.01) | |
| *G01N 33/53* | (2006.01) | |
| *C12Q 1/60* | (2006.01) | |
| *G01N 21/27* | (2006.01) | |
| *G01N 33/52* | (2006.01) | |

(52) U.S. Cl.
CPC ........ *G01N 33/92* (2013.01); *B01L 3/502707* (2013.01); *B01L 3/502715* (2013.01); *B01L 3/502753* (2013.01); *C12Q 1/60* (2013.01); *G01N 21/27* (2013.01); *G01N 21/31* (2013.01); *G01N 33/525* (2013.01); *G01N 33/5302* (2013.01); *B01L 2200/0605* (2013.01); *B01L 2200/0631* (2013.01); *B01L 2200/10* (2013.01); *B01L 2300/0654* (2013.01); *B01L 2300/087* (2013.01); *B01L 2300/0819* (2013.01); *B01L 2300/0874* (2013.01); *B01L 2300/0887* (2013.01); *B01L 2300/168* (2013.01); *G01N 2201/061* (2013.01); *G01N 2201/062* (2013.01); *Y10T 436/20* (2015.01)

(58) Field of Classification Search
None
See application file for complete search history.

(56) References Cited

U.S. PATENT DOCUMENTS

| | | |
|---|---|---|
| 4,003,379 A | 1/1977 | Ellinwood, Jr. |
| 4,146,029 A | 3/1979 | Ellinwood, Jr. |
| 4,347,176 A | 8/1982 | Mehta |
| 4,731,726 A | 3/1988 | Allen, III |
| 4,793,825 A | 12/1988 | Benjamin et al. |
| 4,910,131 A | 3/1990 | Mellman et al. |
| 4,920,213 A | 4/1990 | Dale et al. |
| 4,946,795 A | 8/1990 | Gibbons et al. |
| 5,089,229 A | 2/1992 | Heidt et al. |
| 5,104,813 A | 4/1992 | Besemer et al. |
| 5,130,238 A | 7/1992 | Malek et al. |
| 5,162,237 A | 11/1992 | Messenger et al. |
| 5,270,184 A | 12/1993 | Walker et al. |
| 5,273,905 A | 12/1993 | Muller et al. |
| 5,279,607 A | 1/1994 | Schentag et al. |
| 5,281,395 A | 1/1994 | Markart et al. |
| 5,380,487 A | 1/1995 | Choperena et al. |
| 5,443,790 A | 8/1995 | Coeurveille et al. |
| 5,455,166 A | 10/1995 | Walker |
| 5,472,603 A | 12/1995 | Schembri |
| 5,527,670 A | 6/1996 | Stanley |
| 5,554,539 A | 9/1996 | Chadney et al. |
| 5,578,269 A | 11/1996 | Yaremko et al. |
| 5,624,850 A | 4/1997 | Kumar et al. |
| 5,648,211 A | 7/1997 | Fraiser et al. |
| 5,670,375 A | 9/1997 | Seaton et al. |

(Continued)

FOREIGN PATENT DOCUMENTS

| | | |
|---|---|---|
| CN | 1146017 A | 3/1997 |
| CN | 1173776 A | 2/1998 |

(Continued)

OTHER PUBLICATIONS

UnifiedPatents blog post dated May 7, 2020, available at https://www.unifiedpatents.com/insights/2020/5/7/1/prior-art-theranos-covid.
UnifiedPatents Patroll Winning Submission; (Holmes I), linked to UnifiedPatents blog post dated May 7, 2020.
UnifiedPatents Patroll Winning Submission; (Holmes II), linked to UnifiedPatents blog post dated May 7, 2020.
Apex Standards Enterprise; Pseudo Claim Charting; U.S. Pat. No. 10,533,994B2, linked to UnifiedPatents blog post dated May 7, 2020.
Apex Standards Enterprise; Pseudo Claim Charting; U.S. Pat. No. 8,283,155B2, linked to UnifiedPatents blog post dated May 7, 2020.
Bawendi, et al. The quantum-mechanics of larger semiconductor clusters. Annu. Rev. Phys. Chem. 1990; 41:477-496.

(Continued)

*Primary Examiner* — Ann Montgomery
(74) *Attorney, Agent, or Firm* — Sterne, Kessler, Goldstein & Fox P.L.L.C.

(57) ABSTRACT

This invention is in the field of medical devices. Specifically, the present invention provides portable medical devices that allow detection of analytes from a biological fluid. The methods and devices are particularly useful for providing point-of-care testing for a variety of medical applications.

19 Claims, 9 Drawing Sheets

(56) References Cited

U.S. PATENT DOCUMENTS

| | | |
|---|---|---|
| 5,674,698 A | 10/1997 | Zarling et al. |
| 5,687,716 A | 11/1997 | Kaufmann et al. |
| 5,693,233 A | 12/1997 | Schembri |
| 5,716,852 A | 2/1998 | Yager et al. |
| 5,744,366 A | 4/1998 | Kricka et al. |
| 5,797,898 A | 8/1998 | Santini et al. |
| 5,801,057 A | 9/1998 | Smart et al. |
| 5,807,375 A | 9/1998 | Gross et al. |
| 5,820,548 A | 10/1998 | Sieben et al. |
| 5,832,296 A | 11/1998 | Wang et al. |
| 5,842,787 A | 12/1998 | Kopf-Sill et al. |
| 5,848,991 A | 12/1998 | Gross et al. |
| 5,854,033 A | 12/1998 | Lizardi |
| 5,863,502 A | 1/1999 | Southgate et al. |
| 5,874,046 A | 2/1999 | Megerle |
| 5,874,214 A | 2/1999 | Nova et al. |
| 5,876,675 A | 3/1999 | Kennedy |
| 5,885,470 A | 3/1999 | Parce et al. |
| 5,891,734 A | 4/1999 | Gill et al. |
| 5,902,549 A | 5/1999 | Mimura et al. |
| 5,939,291 A | 8/1999 | Loewy et al. |
| 5,942,443 A | 8/1999 | Parce et al. |
| 5,961,451 A | 10/1999 | Reber et al. |
| 5,961,923 A | 10/1999 | Nova et al. |
| 5,976,896 A | 11/1999 | Kumar et al. |
| 5,980,830 A | 11/1999 | Savage et al. |
| 6,046,056 A | 4/2000 | Parce et al. |
| 6,074,616 A | 6/2000 | Buechler et al. |
| 6,123,861 A | 9/2000 | Santini, Jr. et al. |
| 6,156,181 A | 12/2000 | Parce et al. |
| 6,168,948 B1 | 1/2001 | Anderson et al. |
| 6,174,675 B1 | 1/2001 | Chow et al. |
| 6,176,962 B1 | 1/2001 | Soane et al. |
| 6,200,814 B1 | 3/2001 | Malmqvist et al. |
| 6,204,068 B1 | 3/2001 | Soini et al. |
| 6,221,677 B1 | 4/2001 | Wu et al. |
| 6,245,057 B1 | 6/2001 | Sieben et al. |
| 6,267,858 B1 | 7/2001 | Parce et al. |
| 6,299,839 B1 | 10/2001 | Karunaratne et al. |
| 6,319,668 B1 | 11/2001 | Nova et al. |
| 6,340,588 B1 | 1/2002 | Nova et al. |
| 6,352,854 B1 | 3/2002 | Nova et al. |
| 6,361,958 B1 | 3/2002 | Shieh et al. |
| 6,368,275 B1 | 4/2002 | Sliwa et al. |
| 6,372,428 B1 | 4/2002 | Nova et al. |
| 6,375,469 B1 | 4/2002 | Brown |
| 6,403,338 B1 | 6/2002 | Knapp et al. |
| 6,429,025 B1 | 8/2002 | Parce et al. |
| 6,440,725 B1 | 8/2002 | Pourahmadi et al. |
| 6,464,687 B1 | 10/2002 | Ishikawa et al. |
| 6,471,916 B1 | 10/2002 | Noblett |
| 6,482,593 B2 | 11/2002 | Walt et al. |
| 6,484,104 B2 | 11/2002 | Abraham-Fuchs et al. |
| 6,491,666 B1 | 12/2002 | Santini, Jr. et al. |
| 6,503,231 B1 | 1/2003 | Prausnitz et al. |
| 6,527,762 B1 | 3/2003 | Santini, Jr. et al. |
| 6,542,717 B1 | 4/2003 | Zimmerman et al. |
| 6,544,732 B1 | 4/2003 | Chee et al. |
| 6,551,838 B2 | 4/2003 | Santini, Jr. et al. |
| 6,591,124 B2 | 7/2003 | Sherman et al. |
| 6,632,216 B2 | 10/2003 | Houzego et al. |
| 6,649,358 B1 | 11/2003 | Parce et al. |
| 6,663,003 B2 | 12/2003 | Johnson et al. |
| 6,664,104 B2 | 12/2003 | Pourahmadi et al. |
| 6,789,510 B1 | 9/2004 | Lee |
| 6,832,296 B2 | 12/2004 | Hooker |
| 6,849,237 B2 | 2/2005 | Housefield et al. |
| 6,878,755 B2 | 4/2005 | Singh et al. |
| 6,887,202 B2 | 5/2005 | Currie et al. |
| 6,893,879 B2 | 5/2005 | Petersen et al. |
| 6,923,764 B2 | 8/2005 | Aceti et al. |
| 6,927,851 B2 | 8/2005 | McCaffrey et al. |
| 6,929,636 B1 | 8/2005 | von Alten |
| 6,949,377 B2 | 9/2005 | Ho |
| 6,966,880 B2 | 11/2005 | Boecker et al. |
| 7,039,453 B2 | 5/2006 | Mullick et al. |
| 7,052,831 B2 | 5/2006 | Fletcher et al. |
| 7,105,183 B2 | 9/2006 | McGrath |
| 7,112,444 B2 | 9/2006 | Beebe et al. |
| 7,178,386 B1 | 2/2007 | Gamble et al. |
| 7,201,872 B2 | 4/2007 | Meron |
| 7,291,497 B2 | 11/2007 | Holmes et al. |
| 7,405,395 B2 | 7/2008 | Ellson et al. |
| 7,459,305 B2 | 12/2008 | Levy |
| 7,635,594 B2 | 12/2009 | Holmes et al. |
| 7,636,667 B2 | 12/2009 | Brown |
| 7,771,658 B2 | 8/2010 | Larsen |
| 7,807,197 B2 | 10/2010 | Lee et al. |
| 7,887,750 B2 | 2/2011 | Blatt et al. |
| 8,055,329 B2 | 11/2011 | Kimchy et al. |
| 8,158,430 B1 | 4/2012 | Roy et al. |
| 8,283,155 B2 | 10/2012 | Holmes et al. |
| 8,394,608 B2 | 3/2013 | Ririe et al. |
| 8,669,047 B2 | 3/2014 | Holmes et al. |
| 8,741,230 B2 * | 6/2014 | Holmes ............ A61B 5/150022 422/50 |
| 8,778,665 B2 * | 7/2014 | Gibbons ................ C12Q 1/60 435/287.2 |
| 8,883,518 B2 | 11/2014 | Roy et al. |
| 9,303,286 B2 * | 4/2016 | Gibbons ........... B01L 3/502753 |
| 10,156,579 B2 * | 12/2018 | Gibbons ................ G01N 33/92 |
| 10,533,994 B2 | 1/2020 | Holmes et al. |
| 2001/0019831 A1 | 9/2001 | Phillips et al. |
| 2001/0045355 A1 | 11/2001 | Gephart et al. |
| 2001/0051340 A1 | 12/2001 | Singh et al. |
| 2001/0051766 A1 | 12/2001 | Gazdzinski |
| 2001/0053535 A1 | 12/2001 | Bashir et al. |
| 2002/0001854 A1 | 1/2002 | Lee |
| 2002/0034757 A1 | 3/2002 | Cubicciotti |
| 2002/0034766 A1 | 3/2002 | Huang et al. |
| 2002/0042125 A1 | 4/2002 | Petersen et al. |
| 2002/0055094 A1 | 5/2002 | Reece et al. |
| 2002/0055127 A1 | 5/2002 | Gindilis |
| 2002/0055167 A1 | 5/2002 | Pourahmadi et al. |
| 2002/0059030 A1 | 5/2002 | Otworth et al. |
| 2002/0072733 A1 | 6/2002 | Flaherty |
| 2002/0092770 A1 | 7/2002 | Hedberg et al. |
| 2002/0110496 A1 | 8/2002 | Samsoondar |
| 2002/0114739 A1 | 8/2002 | Weigl et al. |
| 2002/0120183 A1 | 8/2002 | Abraham-Fuchs et al. |
| 2002/0120187 A1 | 8/2002 | Eiffert et al. |
| 2002/0132226 A1 | 9/2002 | Nair et al. |
| 2002/0143437 A1 | 10/2002 | Handique et al. |
| 2002/0187074 A1 * | 12/2002 | O'Connor ............ B01J 19/0093 422/502 |
| 2003/0012692 A1 | 1/2003 | Lemee et al. |
| 2003/0014362 A1 | 1/2003 | Yim |
| 2003/0049833 A1 | 3/2003 | Chen et al. |
| 2003/0049865 A1 | 3/2003 | Santini et al. |
| 2003/0061687 A1 | 4/2003 | Hansen et al. |
| 2003/0069560 A1 | 4/2003 | Adamis et al. |
| 2003/0097092 A1 | 5/2003 | Flaherty |
| 2003/0104590 A1 | 6/2003 | Santini et al. |
| 2003/0113713 A1 | 6/2003 | Glezer et al. |
| 2003/0114735 A1 | 6/2003 | Silver et al. |
| 2003/0117491 A1 | 6/2003 | Avni et al. |
| 2003/0143551 A1 | 7/2003 | Cattell |
| 2003/0148362 A1 | 8/2003 | Luka |
| 2003/0153900 A1 | 8/2003 | Aceti et al. |
| 2003/0167000 A1 | 9/2003 | Mullick et al. |
| 2003/0185706 A1 | 10/2003 | Ribi |
| 2003/0191430 A1 | 10/2003 | D'Andrea et al. |
| 2003/0208113 A1 | 11/2003 | Mault et al. |
| 2003/0208133 A1 | 11/2003 | Mault |
| 2003/0210607 A1 | 11/2003 | Gilbert et al. |
| 2003/0211007 A1 | 11/2003 | Maus et al. |
| 2003/0211618 A1 | 11/2003 | Patel |
| 2003/0212379 A1 | 11/2003 | Bylund et al. |
| 2003/0214057 A1 | 11/2003 | Huang |
| 2004/0005247 A1 | 1/2004 | Karp |
| 2004/0005582 A1 | 1/2004 | Shipwash |
| 2004/0014202 A1 | 1/2004 | King et al. |
| 2004/0033553 A1 | 2/2004 | Littarru et al. |
| 2004/0053290 A1 | 3/2004 | Terbrueggen et al. |

(56) References Cited

U.S. PATENT DOCUMENTS

| | | |
|---|---|---|
| 2004/0086872 A1 | 5/2004 | Childers et al. |
| 2004/0096959 A1 | 5/2004 | Stiene et al. |
| 2004/0109793 A1 | 6/2004 | McNeely et al. |
| 2004/0121305 A1 | 6/2004 | Wiegand et al. |
| 2004/0122486 A1 | 6/2004 | Stahmann et al. |
| 2004/0213825 A1 | 10/2004 | Levy |
| 2004/0228766 A1 | 11/2004 | Witty et al. |
| 2004/0260204 A1 | 12/2004 | Boecker et al. |
| 2005/0009101 A1 | 1/2005 | Blackburn |
| 2005/0009191 A1 | 1/2005 | Swenson et al. |
| 2005/0019836 A1 | 1/2005 | Vogel et al. |
| 2005/0054078 A1 | 3/2005 | Miller et al. |
| 2005/0064529 A1 | 3/2005 | Kwon |
| 2005/0090726 A1 | 4/2005 | Ackerman |
| 2005/0100937 A1* | 5/2005 | Holmes ............... A61B 5/14556 435/6.12 |
| 2005/0106713 A1 | 5/2005 | Phan et al. |
| 2005/0112544 A1 | 5/2005 | Xu et al. |
| 2005/0130292 A1 | 6/2005 | Ahn et al. |
| 2005/0130321 A1 | 6/2005 | Nicholson et al. |
| 2005/0136548 A1 | 6/2005 | Mcdevitt et al. |
| 2005/0137481 A1 | 6/2005 | Sheard et al. |
| 2005/0147559 A1 | 7/2005 | von Alten |
| 2005/0209565 A1 | 9/2005 | Yuzhakov et al. |
| 2005/0221281 A1 | 10/2005 | Ho |
| 2005/0249633 A1 | 11/2005 | Blatt et al. |
| 2005/0255001 A1 | 11/2005 | Padmanabhan et al. |
| 2005/0255600 A1 | 11/2005 | Padmanabhan et al. |
| 2006/0018795 A1 | 1/2006 | Potyrailo et al. |
| 2006/0019319 A1 | 1/2006 | Billadeau et al. |
| 2006/0029924 A1 | 2/2006 | Brewster et al. |
| 2006/0062852 A1 | 3/2006 | Holmes |
| 2006/0078998 A1 | 4/2006 | Puskas et al. |
| 2006/0106316 A1 | 5/2006 | Palti |
| 2006/0177873 A1 | 8/2006 | Dowd et al. |
| 2006/0182738 A1 | 8/2006 | Holmes |
| 2006/0211933 A1 | 9/2006 | Zimmermann et al. |
| 2006/0257941 A1 | 11/2006 | McDevitt et al. |
| 2006/0264779 A1 | 11/2006 | Kemp et al. |
| 2006/0264780 A1 | 11/2006 | Holmes et al. |
| 2006/0264781 A1 | 11/2006 | Gibbons et al. |
| 2006/0264782 A1 | 11/2006 | Holmes et al. |
| 2006/0264783 A1 | 11/2006 | Holmes et al. |
| 2007/0059196 A1 | 3/2007 | Brister et al. |
| 2007/0166195 A1 | 7/2007 | Padmanabhan et al. |
| 2007/0207060 A1* | 9/2007 | Zou .................. G01N 21/6452 422/68.1 |
| 2007/0224084 A1 | 9/2007 | Holmes et al. |
| 2007/0264629 A1 | 11/2007 | Holmes et al. |
| 2008/0009766 A1 | 1/2008 | Holmes et al. |
| 2008/113391 A1 | 5/2008 | Gibbons et al. |
| 2010/0074799 A1 | 3/2010 | Kemp et al. |
| 2010/0081144 A1 | 4/2010 | Holmes et al. |
| 2011/0003699 A1 | 1/2011 | Yoder et al. |
| 2011/0104826 A1 | 5/2011 | Gibbons et al. |
| 2011/0166553 A1 | 7/2011 | Holmes et al. |
| 2012/0034598 A1 | 2/2012 | Holmes et al. |
| 2012/0258472 A1 | 10/2012 | Roy et al. |
| 2013/0115685 A1 | 5/2013 | Holmes et al. |

FOREIGN PATENT DOCUMENTS

| | | | |
|---|---|---|---|
| CN | 1253625 A | 5/2000 | |
| CN | 1262606 A | 8/2000 | |
| CN | 1415964 A | 5/2003 | |
| CN | 1416528 A | 5/2003 | |
| CN | 2559986 Y | 7/2003 | |
| CN | 1499949 A | 5/2004 | |
| CN | 1526074 A | 9/2004 | |
| CN | 1173776 C | 11/2004 | |
| CN | 1572320 A | 2/2005 | |
| CN | 1192567 C | 3/2005 | |
| CN | 1746675 A | 3/2006 | |
| EP | 0478319 A1 | 4/1992 | |
| EP | 0541340A 2 | 5/1993 | |
| EP | 0564254 A1 | 10/1993 | |
| EP | 0571225 A2 | 11/1993 | |
| EP | 0576602 A1 | 1/1994 | |
| EP | 0631137 A2 | 12/1994 | |
| EP | 0636685 A2 | 2/1995 | |
| EP | 0637996 A1 | 2/1995 | |
| EP | 0637998 A1 | 2/1995 | |
| EP | 0639223 A1 | 2/1995 | |
| EP | 0640826 A1 | 3/1995 | |
| EP | 0640828 A1 | 3/1995 | |
| EP | 0652600 A1 | 5/1995 | |
| EP | 0684315 A1 | 11/1995 | |
| EP | 0693560 A2 | 1/1996 | |
| EP | 0723146 A1 | 7/1996 | |
| EP | 0734017 A1 | 9/1996 | |
| EP | 0844475 A2 | 5/1998 | |
| EP | 0962773 A1 | 12/1999 | |
| EP | 0971039 A2 | 1/2000 | |
| EP | 1002229 A1 | 5/2000 | |
| EP | 1086719 A1 | 3/2001 | |
| EP | 1106244 A2 | 6/2001 | |
| EP | 1174078 A2 | 1/2002 | |
| EP | 1202057 A2 | 5/2002 | |
| EP | 1203959 A1 | 5/2002 | |
| EP | 1225442 A2 | 7/2002 | |
| EP | 1346686 A2 | 9/2003 | |
| EP | 1360931 A1 | 11/2003 | |
| EP | 1415788 A1 | 5/2004 | |
| EP | 1498067 A1 | 1/2005 | |
| JP | H0727700 A | 1/1995 | |
| JP | H07103959 A | 4/1995 | |
| JP | H07120393 A | 5/1995 | |
| JP | H07151101 A | 6/1995 | |
| JP | H07196314 A | 8/1995 | |
| JP | H07304799 A | 11/1995 | |
| JP | H08211071 A | 8/1996 | |
| JP | H08334505 A | 12/1996 | |
| JP | H0968533 A | 3/1997 | |
| JP | H0980021 A | 3/1997 | |
| JP | H09113511 A | 5/1997 | |
| JP | H09192218 A | 7/1997 | |
| JP | H09244055 A | 9/1997 | |
| JP | H09253056 A | 9/1997 | |
| JP | H09281078 A | 10/1997 | |
| JP | H1072628 A | 3/1998 | |
| JP | H10132712 A | 5/1998 | |
| JP | H10239240 A | 9/1998 | |
| JP | H10267888 A | 10/1998 | |
| JP | H10305016 A | 11/1998 | |
| JP | H1157560 A | 3/1999 | |
| JP | H11352094 A | 12/1999 | |
| JP | 2000303067 | * 10/2000 | ............ C09K 11/07 |
| JP | 2000314719 A | 11/2000 | |
| JP | 2001065458 A | 3/2001 | |
| JP | 2001157855 A | 6/2001 | |
| JP | 2001165752 A | 6/2001 | |
| JP | 2001319560 A | 11/2001 | |
| JP | 2002010990 A | 1/2002 | |
| JP | 2002031055 A | 1/2002 | |
| JP | 2002041654 A | 2/2002 | |
| JP | 2002044007 A | 2/2002 | |
| JP | 2002511965 A | 4/2002 | |
| JP | 2002161856 A | 6/2002 | |
| JP | 2002263185 A | 9/2002 | |
| JP | 2002266762 A | 9/2002 | |
| JP | 2002282217 A | 10/2002 | |
| JP | 2002538440 A | 11/2002 | |
| JP | 2002371955 A | 12/2002 | |
| JP | 2003057244 A | 2/2003 | |
| JP | 2003166910 A | 6/2003 | |
| JP | 2003167960 A | 6/2003 | |
| JP | 2003207454 A | 7/2003 | |
| JP | 2003222611 A | 8/2003 | |
| JP | 2003315348 A | 11/2003 | |
| JP | 2003322653 A | 11/2003 | |
| JP | 2003329696 A | 11/2003 | |
| JP | 2004028589 A | 1/2004 | |
| JP | 2004101381 A | 4/2004 | |

(56) References Cited

FOREIGN PATENT DOCUMENTS

| | | | |
|---|---|---|---|
| JP | 2004527825 A | 9/2004 | |
| JP | 2004317498 A | 11/2004 | |
| JP | 2004333452 A | 11/2004 | |
| JP | 2004358261 A | 12/2004 | |
| JP | 2005010179 A | 1/2005 | |
| JP | 2005015243 A | 1/2005 | |
| JP | 2005030983 A | 2/2005 | |
| JP | 2005104750 A | 4/2005 | |
| JP | 2005130855 A | 5/2005 | |
| JP | 2005140681 A | 6/2005 | |
| JP | 2005291954 A | 10/2005 | |
| JP | 2007187677 A | 7/2007 | |
| WO | WO 94/01165 A1 | 1/1994 | |
| WO | WO 00/78454 A1 | 12/2000 | |
| WO | WO 01/35928 A1 | 5/2001 | |
| WO | WO 01/64344 A2 | 9/2001 | |
| WO | WO 02/064038 A2 | 8/2002 | |
| WO | WO 02/064826 A2 | 8/2002 | |
| WO | WO 03/066128 A2 | 8/2003 | |
| WO | WO 2005/024437 A1 | 3/2005 | |
| WO | WO 2005/025413 A2 | 3/2005 | |
| WO | WO 2005/031355 A1 | 4/2005 | |
| WO | WO 2005059553 * | 6/2005 | G01N 33/543 |
| WO | WO 2005/065157 A2 | 7/2005 | |
| WO | WO 2005/065538 A2 | 7/2005 | |
| WO | WO2005074161 A1 | 8/2005 | |
| WO | WO 2005/121367 A1 | 12/2005 | |
| WO | WO 2007/120904 A2 | 10/2007 | |

OTHER PUBLICATIONS

BD Biosciences, Directigen FluA&B Assay Manual. Oct. 11, 2016, pp. 1-11.
Beier, et al. Versatile derivatisation of solid support media for covalent bonding on DNA-microchips. Nucleic Acids Res. 1999; 27:1970-1977.
Bes, et al. Mapping the paratope of anti-CD4 recombinant Fab 13B8.2 by combining parallel peptide synthesis and site-directed mutagenesis. J Biol Chem. Apr. 18, 2003;278(16):14265-73.
Bhatia, et al. Use of thiol-terminal silanes and heterobifuntional crosslinkers for immobilization of antibodies on silica surfaces. Anal Biochem. 1989; 178(2):408-13.
Broadcaster Moira Gunn with Elizabeth Holmes, recorded Mar. 5, 2005 on Biotech Nation.
Bruchez, et al. Semiconductor nanocrystals as fluorescent biological labels. Science. 1998; 281(5385):2013-6.
Celebre, et al. A comparative study of efficiencies of fibre optic and prism TIRF sensors. Meas. Sci. Technol. 1992; 3:1166-1173.
Chan. Quantum dot bioconjugates for ultrasensitive nonisotopic detection. Science. 1998;281(5385):2016-8.
Chang, et al. Micromachining & Microfabrication. SPIE Optical Engineering Press. Bellingham, Wash. 1997. (Cover pages and table of contents only).
Charles, et al. Synthesis of a fluorescent analog of polychlorinated biphenyls for use in a continuous flow immunosensor assay. Bioconjug Chem. 1995; 6(6):691-4.
Duffy, et al. Rapid Prototyping of Microfluidic Systems in Poly(dimethylsiloxane). Analytical Chemistry. 1998; 70(23);4974-4084.
European search report and search opinion dated Mar. 6, 2012 for EP Application No. 10179887.4.
European search report and search opinion dated May 29, 2012 for EP Application No. 11180769.9.
European search report dated Jun. 2, 2009 for Application No. 07762092.
Filippini et al. LCD-aided computer screen photo-assisted technique for colorimetric assays evaluation, 2004, Sensors and Actuators B, 103: pp. 158-164.
Gavin, et al. Review of Rapid Diagnostic Tests for Influenza. Clinical and Applied Immunology Reviews. 2004; 4(3)151-172.

Geddes, et al. The impedance of stainless-steel electrodes. Med Biol Eng. Sep. 1971;9(5):511-21.
Harlow, et al. Antibodies: A Laboratory Manual. Cold Spring Harbor Laboratory. New York. 1988. (Cover pages and table of contents only).
Harrison's Principles of Internal Medicine, Part 2 Cardinal Manifestations of Disease, Ch. 60 (12th ed. 1991; pp. 338-343.).
Hendricks et al. An enzyme coupled colorimetric assay for S-adenosylmethionine dependent methyltransferases. Analytical Biochemistry 326 (2004) 100-105.
Hirsh, et al. The electrical conductivity of blood. I: Relationship to erythrocyte concentration. Blood. Nov. 1950;5(11)1017-35.
International search report and written opinion dated Sep. 16, 2008 for PCT/US2007/009878.
International search report dated Jan. 22, 2008 for PCT/US06/42563.
International search report dated Dec. 8, 2008 for PCT/US06/11090.
International search report dated Jul. 4, 2005 for PCT/US04/029462.
International search report dated Aug. 11, 2008 for PCT/US07/68665.
International search report dated Sep. 9, 2008 for PCT/US07/23904.
Jaeger. Introduction to Microelectronic fabrication. Addison-Wesley Publishing Co. Reading Mass. 1988. (Cover pages and table of Contents only).
Kessler, et al. Use of the DNA flow-thru chip, a three-dimensional biochip, for typing and subtyping of influenza viruses. J Clin Microbiol. May 2004;42(5):2173-85.
Khan, et al. Detection of influenza virus neuraminidase-specific antibodies by an enzyme-linked immunosorbent assay. J Clin Microbiol. Jul. 1982; 16(1): 115-22.
Kilbourne, et al. Independent and disparate evolution in nature of influenza A virus hemagglutinin and neuraminidase glycoproteins. Proc Natl Acad Sci U S A. Jan. 1990;87(2):786-90.
Lee, et al. Microfluidic enzyme-linked immunosorbent assay technology. Adv Clin Chem. 2006;42:255-95.
Liu, et al. Validation of a folly integrated microfluidic array device for influenza A subtype identification and sequencing. Anal Chem. Jun. 15, 2006;78(12):4184-93.
Loizou et al. measurement of anti-cardiolipin antibodies by an enzyme-linked immunosorbent assay (ELISA): standardization and quantization of results, 1985, Clin exp Immunol, 62: pp. 738-745.
Lupiani, et al. Improved diagnostic tests for Avian influenza surveillance, 2005, Proceedings of the Institute of Food Technologies' First Annual Forod protection and Defense Research Conference.
Mohapatra, et al. Blood resistivity and its implications for the calculation of cardiac output by the thoracic electrical impedance technique. Intensive Care Med. Aug. 1977;3(2):63-7.
Mukerjee, et al. Microneedle array for transdermal biological fluid extraction and in situ analysis. Sensors and Actuators A. 2004; 114:267-275.
Neelakantaswamy et al. Conductimetric experiment to assay the haemoglobin content of blood, 1984, Med Bio Eng Comp, 22:pp. 367-370.
Notice of Allowance dated Oct. 6, 2015 for U.S. Appl. No. 14/285,562.
Notice of Allowance dated Dec. 3, 2015 for U.S. Appl. No. 14/285,562.
Office Action dated Jan. 5, 2010 for U.S. Appl. No. 11/388,415.
Office Action dated Jan. 8, 2013 for U.S. Appl. No. 11/388,415.
Office Action dated Oct. 17, 2008 for U.S. Appl. No. 11/389,410.
Office Action dated Oct. 26, 2006 for U.S. Appl. No. 10/937,872.
Office Action dated Oct. 31, 2013 for U.S. Appl. No. 12/986,954.
Office Action dated Oct. 6, 2008 for U.S. Appl. No. 11/746,535.
Office Action dated Nov. 22, 2011 for U.S. Appl. No. 11/202,231.
Office Action dated Nov. 5, 2009 for U.S. Appl. No. 11/202,231.
Office Action dated Nov. 9, 2011 for U.S. Appl. No. 11/388,823.
Okamatsu, et al. Epitope mapping of H9N2 influenza virus hemagglutinin and neuraminidase molecule. The Japanese Society of Veterinary Science, Journal of Veterinary Medical Science, Presentation Abstracts, 2004, vol. 137, p. 91, DV-05.
Pal, et al. An integrated microfluidic device for influenza and other genetic analyses. Lab Chip. Oct. 2005;5(10):1024-32. Epub Aug. 18, 2005.

(56) References Cited

OTHER PUBLICATIONS

Patolsky, et al. Electrical detection of single viruses. Proc Natl Acad Sci USA. Sep. 28, 2004;101(39):14017-22. Epub Sep. 13, 2004.
Pescovitz, D. Sniffing out airborne disease. Lab Note: Research from the College of Engineering, University of California, Berkeley, 2004. Available online at http://www.coe.berkeley.edu/labnotes/0904/pisano.html. Accessed Jan. 28, 2011.
Preininger, et al. Polymer-coated optical fibres for application in a direct evanescent wave immunoassay. Analytica Chimica Acta, 2000; 403; 67-76.
Rai-Choudhury, ed., Handbook of Microlithography, Micromachining & Microfabrication. SPIE Optical Engineering Press. Bellingham, Wash. 1997. (Cover pages and table of contents only).
Ray, et al. Distinct hemagglutinin and neuraminidase epitopes involved in antigenic variation of recent human parainfluenza virus type 2 isolates. Virus Res. Jun. 1992;24(1):107-13.
Red Herring. Stopping bad reactions. Red Herring. Dec. 26, 2005.
Runyan, et al. Semiconductor integrated circuit processing technology. Addison-Wesley Publishing Co., Reading Mass. 1990. (Cover pages and table of contents only).
Sambrook, et al. Molecular Cloning: A Laboratory Manual. Cold Spring Harbor Laboratory Press. New York. 2001. (Cover pages and table of contents only).
Sapsford, et al. Demonstration of four immunoassay formats using the array biosensor. Anal Chem. 2002; 74(5):1061-8.
Scheurle, et al. HER-2/neu expression in archival non-small cell lung carcinomas using FDA-approved hercep test. Anticancer Res. 2000; 20:2091-2096.
Spira, et al. The identification of monoclonal class switch variants by sib selection and an ELISA assay. J Immunol Methods. 1984;74(2):307-15.
Steplewski, et al. Isolation and characterization of anti-monosialoganglioside monoclonal antibody 19-9 class-switch variants. Proc Natl Acad Sci U S A. 1985; 82(24):8653-7.
Stevens, et al. Glycan microarray analysis of the hemagglutinins from modem and pandemic influenza viruses reveals different receptor specificities. J Mol Biol. Feb. 3, 2006;355(5):1143-55.
Tedeschi, et al. Antibody immobilisation on fibre optic TIRF sensors. Biosens Bioelectron. 2003; 19(2):85-93.
Yan, et al. Multiplexed flow cytometric immunoassay for influenza virus detection and differentiation. Anal Chem. Dec. 1, 2005;77(23):7673-8.
Office Action dated Dec. 19, 2008 for U.S. Appl. No. 11/202,206.
Office Action dated Dec. 22, 2009 for U.S. Appl. No. 11/388,823.
Office Action dated Dec. 22, 2010 for U.S. Appl. No. 11/554,509.
Office Action dated Feb. 1, 2013 for U.S. Appl. No. 13/187,960.
Office Action dated Feb. 17, 2009 for U.S. Appl. No. 11/202,231.
Office Action dated Feb. 2, 2011 for U.S. Appl. No. 11/746,535.
Office Action dated Feb. 22, 2008 for U.S. Appl. No. 11/202,231.
Office Action dated Feb. 22, 2008 for U.S. Appl. No. 11/746,535.
Office Action dated Feb. 27, 2009 for U.S. Appl. No. 11/388,723.
Office Action dated Mar. 16, 2011 for U.S. Appl. No. 11/202,231.
Office Action dated Mar. 17, 2009 for U.S. Appl. No. 11/388,415.
Office Action dated Mar. 18, 2008 for U.S. Appl. No. 11/202,206.
Office Action dated Mar. 21, 2008 for U.S. Appl. No. 11/388,723.
Office Action dated Mar. 21, 2011 for U.S. Appl. No. 11/388,415.
Office Action dated Mar. 22, 2010 for U.S. Appl. No. 11/202,206.
Office Action dated Mar. 3, 2011 for U.S. Appl. No. 11/202,206.
Office Action dated Mar. 5, 2009 for U.S. Appl. No. 11/388,823.
Office Action dated Mar. 5, 2010 for U.S. Appl. No. 11/746,535.
Office Action dated Mar. 7, 2006 for U.S. Appl. No. 10/937,872.
Office Action dated Apr. 1, 2010 for U.S. Appl. No. 11/388,824.
Office Action dated Apr. 13, 2012 for U.S. Appl. No. 11/554,509.
Office Action dated Apr. 18, 2007 for U.S. Appl. No. 10/937,872.
Office Action dated Apr. 29, 2009 for U.S. Appl. No. 11/389,409.
Office Action dated Apr. 30, 2009 for U.S. Appl. No. 11/388,824.
Office Action dated Apr. 30, 2013 for U.S. Appl. No. 13/647,325.
Office Action dated Apr. 4, 2013 for U.S. Appl. No. 12/986,954.
Office Action dated Apr. 5, 2010 for U.S. Appl. No. 11/554,509.
Office Action dated Apr. 8, 2009 for U.S. Appl. No. 11/389,410.
Office Action dated May 22, 2009 for U.S. Appl. No. 11/746,535.
Office Action dated May 29, 2012 for U.S. Appl. No. 12/986,954.
Office Action dated Jun. 1, 2007 for U.S. Appl. No. 11/389,409.
Office Action dated Jun. 1, 2012 for U.S. Appl. No. 11/388,823.
Office Action dated Jun. 11, 2012 for U.S. Appl. No. 11/388,415.
Office Action dated Jun. 21, 2007 for U.S. Appl. No. 11/202,231.
Office Action dated Jun. 24, 2013 for U.S. Appl. No. 13/436,568.
Office Action dated Jun. 9, 2010 for U.S. Appl. No. 11/746,535.
Office Action dated Jul. 18, 2012 for U.S. Appl. No. 12/576,197.
Office Action dated Jul. 25, 2008 for U.S. Appl. No. 11/389,409.
Office Action dated Jul. 27, 2011 for U.S. Appl. No. 11/554,509.
Office Action dated Jul. 28, 2009 for U.S. Appl. No. 11/202,206.
Office Action dated Jul. 29, 2011 for U.S. Appl. No. 12/986,954.
Office Action dated Aug. 24, 2010 for U.S. Appl. No. 11/388,415.
Office Action dated Aug. 27, 2010 for U.S. Appl. No. 11/388,823.
Office Action dated Aug. 29, 2008 for U.S. Appl. No. 11/388,823.
Office Action dated Aug. 31, 2011 for U.S. Appl. No. 12/221,816.
Office Action dated Sep. 1, 2005 for U.S. Appl. No. 10/937,872.
Office Action dated Sep. 11, 2008 for U.S. Appl. No. 11/389,409.
Office Action dated Sep. 22, 2011 for U.S. Appl. No. 12/576,197.
Office Action dated Sep. 4, 2013 for U.S. Appl. No. 11/388,823.
Office Action dated Sep. 5, 2008 for U.S. Appl. No. 11/388,723.
Von Schenck, H., et al., "Evaluation of "HemoCue," a New Device for Determining Hemoglobin," Clin Chem., vol. 32(3): 526-529 (1986).
Neufeld, L., et al., "Hemoglobin measured by Hemocue and a reference method in venous and capillary blood: A validation study," Salud Publica de Mexico, vol. 44(3): 219-227 (2002).
HemoCue Hb 201+ Operating Manual, HomeCue AB, Angelholm Sweden, www.hemocue.com.
Cheng, S. B., et al., "Development of a Multichannel Microfluidic Analysis System Employing Affinity Capillary Electrophoresis for Immunoassay," Anal. Chem., vol. 73(7): 1472-1479 (2001).
Clayton, J., "Go with the microflow," Nature Methods, vol. 2(8): 621-627 (2005).
Hong, J. W., et al., "A nanoliter-scale nucleic acid processor with parallel architecture," Nature Biotechnology, vol. 22(4): 435-439 (2004).

\* cited by examiner

METHODS FOR THE DETECTION OF ANALYTES IN SMALL-VOLUME BLOOD SAMPLES

CROSS-REFERENCE TO RELATED APPLICATION

This application is a continuation application of U.S. Ser. No. 15/054,510, filed on Feb. 26, 2016, which is a continuation of U.S. Ser. No. 14/285,562, filed on May 22, 2014, which is a divisional of U.S. Ser. No. 12/750,518, filed Mar. 30, 2010, which is a continuation of U.S. Ser. No. 11/939,509, filed on Nov. 13, 2007, which claims the benefit of U.S. Provisional Application No. 60/865,805 filed Nov. 14, 2006. Each of these applications is incorporated herein by reference in its entirety.

BACKGROUND OF THE INVENTION

Many medical procedures require tests to be performed with a sample of a patient's fluid. The ability to rapidly and accurately detect a wide range of analytes present in a bodily fluid is often critical for diagnosis, prognosis, and treatment of diseases.

Traditionally, detecting a range of analytes present in a bodily fluid such as blood has been performed in laboratories by trained technicians. Performing such assays is usually time-consuming and costly. The desire for rapid turnaround time creates a need to facilitate testing that can be delivered at the point-of-care. Point-of-care testing is particularly desirable because it rapidly delivers results to medical practitioners, enables faster consultation, and avoids unattended deterioration of a patient's condition.

Although several point of care testing devices are available, the majority of which is adapted to detect a single analyte, or one type of analytes for a single indication. Examples of such point of care devices are tests for glucose, drugs of abuse, serum cholesterol, pregnancy, or ovulation.

Thus, there remains a need for alternative designs of point of care systems that are capable of detecting a range of analytes from bodily fluid. A desirable system would allow quantitative and qualitative measurements of analytes in a more cost effective and timely fashion. The present invention addresses this need and provides related advantages as well.

SUMMARY OF THE INVENTION

One aspect of the present invention is the design of a system to effect detection of different analytes in a bodily fluid. In one embodiment, the present invention provides a system that typically comprises a) a fluidic device comprising a cartridge, said cartridge comprising a sample collection unit and an assay assembly, wherein said sample collection unit allows a sample of bodily fluid to react with reactants contained within said assay assembly to yield a colored product having an absorbance spectrum corresponding to at least one wavelength from a light source; b) a light source transmitting the at least one wavelength to the assay assembly; and c) a detector that detects absorption of light of the at least one wavelength, wherein said absorption is indicative of the presence of the analyte in said bodily fluid. In general, the amount of absorption is related to the concentration of the analyte in the bodily fluid. Preferably, the amount of absorption is stoichiometrically related to the concentration of the analyte in the bodily fluid. The subject system is preferably configured to be a point-of-care system.

In a related but separate embodiment, the present invention provides a fluidic device capable of detecting the presence or absence of an analyte in a bodily fluid from a subject. The fluidic device can be part of the system described above. The subject fluidic device typically comprises (a) a cartridge, said cartridge comprising a sample collection unit, an assay assembly, and (b) a light source, wherein said sample collection unit is configured to collect a sample of bodily fluid from said subject and wherein said assay assembly comprises at least one reaction site containing a reactant that reacts with said analyte to yield a colored product having an absorbance spectrum corresponding to at least one wavelength from said light source. Where desired, the fluidic device can be employed to detect a plurality of analytes.

The assay assembly employed in the subject fluidic device or system is generally configured to run an enzymatic assay yielding a colored product. The assay assembly can be configured to run assays capable of detecting a wide variety of analytes. Non-limiting exemplary analytes include drug, drug metabolite, biomarker indicative of a disease, tissue specific marker, and tissue specific enzyme. Preferred analytes for detection include without limitation HDL cholesterol, LDL cholesterol, total cholesterol, lipids, and glucose. Where desired, the assay assembly is configured to run an immunoassay.

The light source employed in the subject fluidic device or system typically produces at least one wavelength corresponding to the absorbance spectrum of the colored product generated by an assay. A suitable light source can comprise a light emitting diode and/or luminescent paint. Where luminescent paint is used as the light source, it is typically coated on the assay assembly.

The present invention also provides a method of detecting an analyte in a bodily fluid from a subject. The method typically involves the steps of a) introducing a sample of bodily fluid into a fluidic device comprising a sample collection unit and an assay assembly, said assay assembly comprising reactants that are capable of reacting with said analytes; b) allowing said sample of bodily fluid to react with said reactants contained within said assay assembly to yield a colored product having an absorbance spectrum corresponding to at least one wavelength from a light source; c) transmitting the at least one wavelength to the fluidic device from said light source; and d) detecting absorption of light of the at least one wavelength transmitted to the fluidic device, wherein said absorption is indicative of the presence of the analyte in said bodily fluid. The method can be employed to detect analytes in a sample of bodily fluid that is less than about 500 ul, less than about 50 ul, or less than about 20 ul, or even less than about 10 ul. Where desired, the methods can be applied to detect analytes in a predetermined amount of bodily fluid that can be undiluted, unprocessed or diluted or processed by, e.g., filtration, centrifugation and other like processes.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

System and Fluidic Device

One aspect of the present invention is a system for detecting an analyte in a sample of bodily fluid from a subject. The terms "subject" and "patient" are used interchangeably herein, which refer to a vertebrate, preferably a mammal, more preferably a human. Mammals include, but are not limited to, murines, simians, humans, farm animals, sport animals, and pets.

The system is capable of detecting and/or quantifying analytes that are associated with specific biological processes, physiological conditions, disorders or stages of disorders.

The subject system typically comprises a fluidic device having one or more of the following components: a sample collection unit, an assay assembly, a light source, a detector, and optionally a communication assembly. In one embodiment, the subject system comprises: a) a fluidic device comprising a cartridge, said cartridge comprising a sample collection unit and an assay assembly, wherein said sample collection unit allows a sample of bodily fluid to react with reactants contained within said assay assembly to yield a colored product having an absorbance spectrum corresponding to at least one wavelength from a light source; b) a light source transmitting the at least one wavelength to the assay assembly; and c) a detector that detects absorption of light of the at least one wavelength, wherein said absorption is indicative of the presence of the analyte in said bodily fluid.

Sample Collection Unit:

The sample collection unit typically allows a sample of bodily fluid to be collected from a subject to react with reactants contained within the assay assembly for generating a signal indicative of the presence of the analyte of interest. The sample collection unit may take a variety of configurations so long as it collects and delivers the sample of bodily fluid to the assay assembly. In some embodiments, the sample collection unit is in fluidic communication with one or more components of the subject system or fluidic device.

Where desired, the sample collection unit is configured to collect a sample of bodily fluid from the subject and to deliver a predetermined portion of the sample to be assayed by the assay assembly. In this manner, the device automatically meters the appropriate volume of the sample that is to be assayed. The sample collection unit can comprise a sample collection well, a metering channel, and a metering element. Generally, the sample collection well collects the bodily fluid from the patient. The metering channel is in fluidic communication with the sample collection well and is dimensioned to collect the predetermined portion of the sample to be assayed. The metering element is adapted to prevent a volume of sample larger than the predetermined portion of the sample from being assayed.

Figure 5:
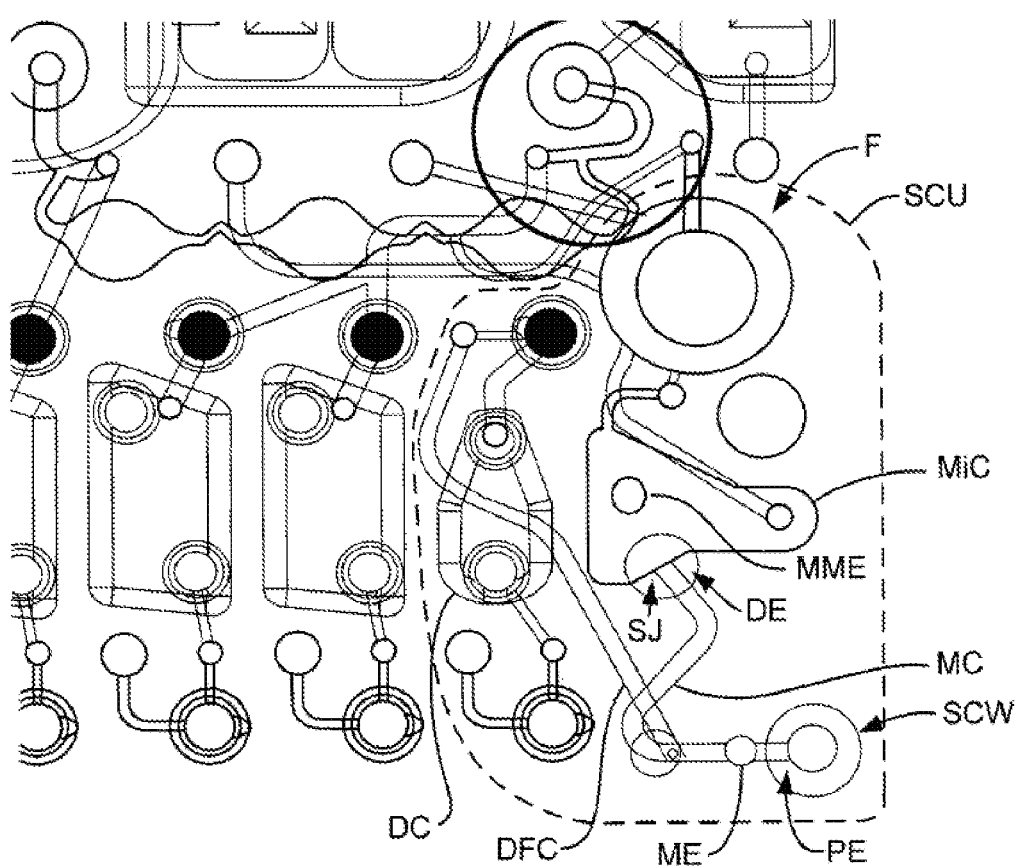
FIG. 5 illustrates an exemplary sample collection unit of the present invention.

FIG. 5 illustrates a top view of an exemplary sample collection unit (SCU) showing sample collection well (SCW) in fluidic communication with metering channel (MC), and metering element (ME).

As shown, the sample collection well (SCW) comprises a through hole with a larger diameter at the top tapering to a smaller diameter at the bottom. The through hole is intended to be the location where the sample is provided to the fluidic device, such as by fingerstick or pipetted blood. The sample collection well (SCW) may be any inlet which allows for a sample to be received by the fluidic device.

The metering channel (ME) can be in fluidic communication with the sample collection well (SCW) to receive the sample. The metering channel (MC) has a proximal end (PE) and a distal end (DE). The distal end (DE) of the metering channel (MC) can include a stop junction (SJ) as will be described below.

In some illustrative embodiments the metering channel (MC) is about 10 mm long and has a cross section of about 1 mm$^2$. In other embodiments the metering channel (MC) is about 12.5 mm long and is about 0.9 mm wide and about 0.9 mm high.

A predetermined portion of sample as used herein can generally refer to the volume of sample inside the metering channel (MC) between the stop junction (SJ) and the metering element (ME) after it has closed the fluidic connection between the sample collection well (SCW) and the metering channel (MC). In some embodiments the dimensions of the metering channel (MC) typically determines the volume of the predetermined portion of sample. The volume of a predetermined portion in a subject sample collection unit (SCU) may be less than 50, less than 40, less than 30 or 20 microliters. In a preferred embodiment, the volume of a predetermined portion is about 10 microliters.

The metering channel (MC) is preferably capable of holding, prior to actuation of the metering element (ME), a volume of sample greater than the predetermined portion such that the stop junction (SJ) does not allow sample to flow into the mixing chamber (MiC) when stressed by a hydrostatic pressure of sample from the sample collection unit (SCU).

Figure 6:
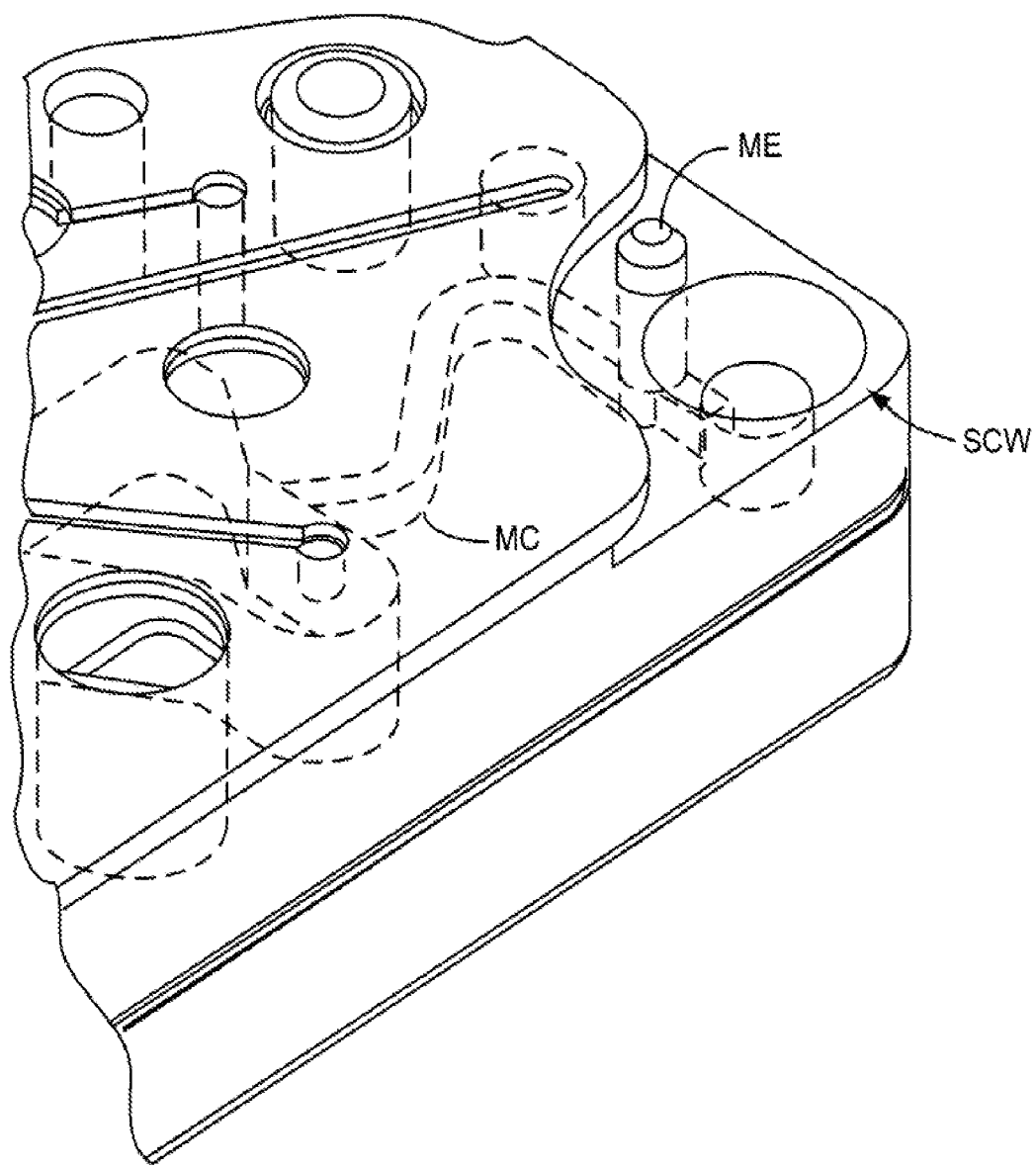
FIG. 6 illustrates an exemplary sample collection well in fluidic communication with a metering channel, and a metering element.

In some embodiments the metering element is adapted to prevent a volume of sample greater than the predetermined portion from being assayed. Generally, the metering element (ME) can be adapted to pinch off the sample inside the metering channel (MC) from the sample collection well (SCW). The metering element (ME) can be a one-time valve initially open and adapted to be actuated by mechanical action by the reader assembly, as described herein. FIG. 6 is a perspective view of the metering element (ME) as a pin shown in an open, or unactuated, position that can be mechanically actuated by the reader assembly to close off the fluidic connection between the sample collection well (SCW) and the metering channel (MC). The metering element (ME) can take any shape and can be of any size, and can be moved into a position to prevent a volume of sample greater than the predetermined portion from being assayed by any technique, e.g., manual force or magnetic force.

In some embodiments the metering channel (MC) has a stop junction (SJ) at its distal end (DE). In FIG. 5, stop junction (SJ) comprises metering channel (MC) opening into the larger mixing chamber (MiC), thereby creating an abrupt end to the capillary dimensions of metering channel (MC). The stop junction (SJ) is shown comprising a right-angled junction between the metering channel (MC) and the mixing chamber (MiC).

The stop junction (SJ) can be adapted to prevent sample from flowing into the mixing chamber (MiC) before the predetermined portion of sample has been metered. While the stop junction (SJ) as shown in FIG. 5 does not comprise any moveable elements, the stop junction (SJ) may also comprise a valve or other blocking element that prevents the predetermined portion of sample from flowing from the metering channel (MC) into the mixing chamber (MiC).

An alternative method of loading the sample into the fluidic device is by side loading rather than loading the sample onto the top of the fluidic device. In such an embodiment, the metering channel (MC) terminates on the side or preferably, at a corner, of the cartridge. The metering channel (MC) can be in direct communication with the mixing chamber (MiC) and the diluent chamber (DC) can be connected by a channel to the metering channel (MC) similar to the top loading embodiment above. The sample can be drawn into the metering channel (MC) by capillary action but does not enter the diluent flush channel (DFC) as that channel is initially sealed from the metering channel (MC). The user or an automated mechanism in the reader assembly then seals the proximal end (PE) of the sample capillary prior to actuating the dilution operation as described above.

In some embodiments the inner surface of the sample collection well (SCW) and/or the metering channel (MC) may be coated with a surfactant and/or an anti-coagulant solution. The surfactant provides a wetting surface to the hydrophobic layers of the fluidic device and facilitate filling of the metering channel (MC) with the fluid sample, e.g., blood, such that the wetness of the metering channel (MC) can not be so large that the stop junction (SJ) cannot contain the blood at the distal end (DE) of the metering channel (MC). The anti-coagulant solution can help prevent the sample, e.g., blood, from clotting when provided to the fluidic device. Exemplary surfactants that can be used include without limitation, Tween, Triton, Pluronic and other non-hemolytic detergents that provide the proper wetting characteristics of a surfactant. EDTA is a non-limiting anti-coagulant that can be used.

In one embodiment the solution comprises 2% Tween, 25 mg/mL EDTA in 50% Methanol/50% $H_2O$, which is then air dried. A methanol/water mixture provides a means of dissolving the EDTA and Tween, and also dries quickly from the surface of the plastic. The solution can be applied to the layers of the fluidic device by any means that will ensure an even film over the surfaces to be coated, such as, e.g., pipetting, spraying, or wicking.

In some embodiments the sample collection unit (SCU) also comprises a dilution chamber (DC) in fluidic communication with the metering channel (MC), wherein the dilution chamber (DC) is configured to store a diluent and comprises a port for engaging pressure means for transferring the diluent from the dilution chamber (DC) into the metering channel (MC). FIG. 5 shows dilution chamber (DC) and diluent flush channel (DFC) fluidly connecting dilution chamber (DC) with the metering channel (MC). The diluent flush channel (DFC) can be adapted to be filled with diluent from the dilution chamber (DC).

In some embodiments the sample collection unit (SCU) further comprises a mixing chamber (MiC) in fluidic communication with the metering channel (MC), wherein the mixing chamber (MiC) is configured to mix the predetermined portion of the sample with the diluent to yield a diluted sample. An exemplary mixing chamber (MiC) is shown in FIG. 5. The mixing chamber (MiC) is preferably dimensioned such that the intersection between the metering channel (MC) and the mixing chamber (MiC) creates a stop junction (SJ) to prevent the predetermined portion of sample from entering the mixing chamber (MiC) until the diluent flushes the sample into the mixing chamber (MiC).

In some embodiments the mixing chamber (MiC) includes a movable mixing element (MME) that causes the mixing of the predetermined portion of the sample with the diluent. Exemplary moveable mixing element (MME) is shown in FIG. 5 with a general ball shape.

In one embodiment the movable mixing element (MME) is magnetically controlled, e.g., a magnetically controlled ball in the mixing chamber (MiC) that, when magnetically controlled, will cause the mixing of the predetermined portion of the sample and the diluent. The ball can be about 5% of the combined volume of the sample and diluent. The ball can be magnetically controlled to move in a reciprocal, linear fashion, within the mixing chamber (MiC).

The moveable mixing element (MME) is shown inside the mixing chamber (MiC), however, it is contemplated that the mixing element may operate outside of the fluidic device, for example when the reader assembly is adapted to agitate the fluidic device and thereby mixing the predetermined portion of sample and the diluent.

In some embodiments the sample collection unit (SCU) further comprises a filter (F) configured to filter the diluted sample before it is assayed. Exemplary filter (F) is shown in FIG. 5. In some embodiments the filter (F) is fluidly connected to and downstream to the mixing chamber (MiC) as shown in FIG. 5.

While the sample collection unit (SCU) can include a dilution chamber (DC), mixing chamber (MiC), and a filter (F), it is contemplated that some or all of these components may not be included in the sample collection unit (SCU). It may, for example, be unnecessary to filter a sample and thus the sample collection unit (SCU) may not have a filter.

Figure 7:
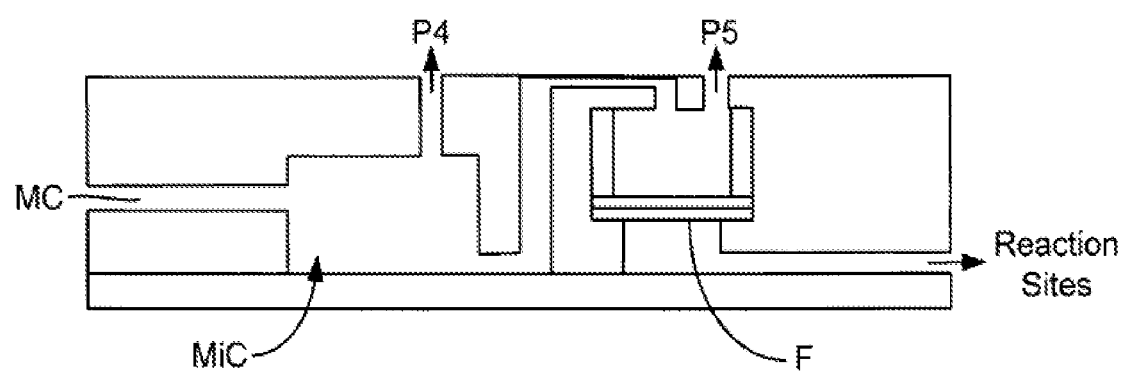
FIG. 7 shows an exemplary fluidic network between a metering channel, a mixing chamber and a filter.

FIG. 7 shows an exemplary fluidic network between a metering channel, a mixing chamber and a filter.

In some embodiments it may be desirable to detect the presence of analytes on a cell surface, within a cell membrane, or inside a cell. The difficulty of detecting such analytes is that cells and other formed elements are particulate and components of cells do not readily interact with traditional assay chemistries which are designed to operate on analytes in solution. Cell-surface analytes react slowly and inefficiently with surface bound probes, and analytes inside the cell can not react at all with bound probes. To allow the detection of such analytes, in some embodiments the fluidic device may include a lysing assembly to lyse cells present in the bodily fluid sample. The lysing assembly may be incorporated with the sample collection unit, a dilution chamber, and/or a filtration chamber. In some embodiments the sample collection unit, dilution chamber, and lysing component are within the same element in the fluidic device. In some embodiments the lysing component may be incorporated with an assay reagent described below.

Where desired, lysing agents may be impregnated and then dried into porous mats, glass fiber mats, sintered frits or particles such as Porex, paper, or other similar material. Lysing agents may be dried onto flat surfaces. Lysing agents may also be dissolved in liquid diluents or other liquid reagents. In some embodiments porous materials are used to store the lysing agents because they can store a lysing agent in dry form likely to be very stable. They can also facilitate the mixing of the bodily fluid sample with the lysing agent by providing a tortuous path for the sample as it moves through the porous material. In some embodiments such porous materials have a disc shape with a diameter greater than its thickness. In some embodiments lysing agents may be dried onto porous materials using lyophilization, passive evaporation, exposure to warm dry flowing gas, or other known methods.

A variety of lysing agents are available in the art and are suitable for use in connection with the subject fluidic device. Preferred lysing agents are non-denaturing, such as non-denaturing detergents. Non-limiting examples of non-denaturing detergents include thesit, sodium deoxylate, triton X-100, and tween-20. The agents are preferably non-volatile in embodiments where the agents are impregnated into a solid porous materials. In some embodiments lysing agents are mixed together. Other materials may be mixed with the lysing agents to modify the lytic effects. Such exemplary materials may be, without limitation, buffers, salts, and proteins. In some embodiments lysing agents will be used in amounts that are in excess of the minimum amount required to lyse cells. In some embodiments lysing agents will be used that can lyse both white and red cells.

The sample collection unit can be adapted to receive any bodily fluids suspected to contain an analyte of interest, such bodily fluids include but are not limited to blood, serum, saliva, urine, gastric and digestive fluid, tears, stool, semen, vaginal fluid, interstitial fluids derived from tumorous tissue, and cerebrospinal fluid.

The volume of bodily fluid to be received in the sample collection unit is generally less than about 500 microliters, or may be less than about 50 microliters.

In some embodiments, the bodily fluids are used directly for detecting the analytes present therein with the subject fluidic device without further processing. Where desired, however, the bodily fluids can be pre-treated before performing the analysis with the subject fluidic devices using any methods described herein or known in the art. The choice of pre-treatments will depend on the type of bodily fluid used and/or the nature of the analyte under investigation. For instance, where the analyte is present at low level in a sample of bodily fluid, the sample can be concentrated via any conventional means to enrich the analyte. Methods of concentrating an analyte include but are not limited to drying, evaporation, centrifugation, sedimentation, precipitation, and amplification. Where the analyte is a nucleic acid, it can be extracted using various lytic enzymes or chemical solutions according to the procedures set forth in Sambrook et al. ("Molecular Cloning: A Laboratory Manual"), or using nucleic acid binding resins following the accompanying instructions provided by manufactures. Where the analyte is a molecule present on or within a cell, extraction can be performed using lysing agents including but not limited to denaturing detergent such as SDS or non-denaturing detergent such as thesit, sodium deoxylate, triton X-100, and tween-20.

In some embodiments, pretreatment can include diluting and/or mixing the sample, and filtering the sample to remove, e.g., red blood cells from a blood sample.

A bodily fluid may be drawn from a patient and brought into the fluidic device in a variety of ways, including but not limited to, lancing, injection, or pipetting. In one embodiment, a lancet punctures the skin and draws the sample into the fluidic device using, for example, gravity, capillary action, aspiration, or vacuum force. The lancet may be part of the fluidic device, or part of a reader assembly, or a stand alone component. In another embodiment where no active mechanism is required, a patient can simply provide a bodily fluid to the fluidic device, as for example, could occur with a saliva sample. The collected fluid can be placed in the sample collection unit within the fluidic device. In yet another embodiment, the fluidic device comprises at least one microneedle which punctures the skin. The microneedle can be used with a fluidic device alone, or can puncture the skin after the fluidic device is inserted into a reader assembly.

A sample collection unit in a fluidic device may provide a bodily fluid sample from a patient by any of the methods described above. If necessary, the sample may first be processed by diluting the bodily fluid in a dilution chamber, and/or may be filtered by separating the plasma from the red blood cells in a filtration chamber as described above. In some embodiments the sample collection unit, diluting chamber, and filtration chamber may be the same component, and in some embodiments they may be different components, or any two may be the same component and the other may be a separate component. In some embodiments there may be more than one sample collection unit in the fluidic device or system.

Assay Assembly:

The assay assembly contained in the subject system or fluidic device comprises reactants capable of reacting with analytes to yield colored products that are indicative of the presence of the analytes. As used herein, the term "analytes" refers to any substances in a bodily fluid that can be used for generating colored products for detection. Exemplary analytes include without limitation drugs, prodrugs, pharmaceutical agents, drug metabolites, a biomarker indicative of a disease, a tissue specific marker, a tissue specific enzyme biomarkers such as expressed proteins and cell markers, antibodies, serum proteins, cholesterol, polysaccharides, nucleic acids, gene, protein, or hormone, or any combination thereof. At a molecular level, the analytes can be polypeptide glycoprotein, polysaccharide, lipid, nucleic acid, and a combination thereof. Preferred detectable analytes include but are not limited to HDL cholesterol, LDL cholesterol, total cholesterol, lipids, glucose, and enzymes.

As noted above, the assay assembly of the subject system or fluidic device is configured to detect analytes based on formation of a colored product from a reaction scheme that is indicative of its presence. Exemplary classes of analytes that can be detected in this manner include: a) analytes that can be converted chemically to a colored product via a color-producing reaction; b) analytes that catalyze the formation of colored products from chemical reactants; and c) analytes that can be detected through binding of an agent that then participates in a color-producing reaction, either as a chemical reagent or a promoter of a chemical reaction. Additional examples of analytes that can yield colored products are illustrated in e.g., Tietz Textbook of Clinical Chemistry (Second Ed., Burtis and Ashwood, Saunders, 1994).

Analytes that can be converted chemically to a colored product via a color-producing reaction include enzyme substrates and co-factors. Non-limiting examples of such analytes include glucose, cholesterol, and triglycerides. In particular, levels of total cholesterol (i.e., the sum of free and esterified cholesterol) in a bodily fluid can be spectrophotometrically measured by well-known color-forming assays by reacting the fluid with reactants including cholesterol esterase, cholesterol oxidase, an oxidizable dye such as n,n-bis(4-sulfobutyl)-3-methylaniline, disodium salt (TODB), 4-aminoantipyrine, and horse radish peroxidase.

A vast number of analytes can catalyze the formation of a colored products from chemical reactants, thus are amenable for detection by optical means. Examples of such analytes include alanine aminotransferase (ALT) and aspartate aminotransferase. Alanine aminotransferase (ALT) is an analyte indicative of liver function. The reactants for use in this assay may include alphaketoglutarate, pyruvate oxidase, an oxidizable dye such as N,N-Bis(4-sulfobutyl)-3-methylaniline, disodium salt (TODB), 4-aminoantipyrine, and horse radish peroxidase.

The third class of analytes is typically detected via a color-producing immunoassay, such as an enzyme-linked immunosorbent assay (ELISA). In a typical ELISA, an analyte is specifically bound by an antibody, which in turn is detected by a secondary, enzyme-linked antibody. The linked enzyme catalyzes a color-producing reaction. Such enzymes include but are not limited to β-galactosidase, alkaline phophatase, and horse radish peroxidase.

The choice of suitable reactants will depend on the particular analytes being examined. In general, any reactants capable of reacting with analytes either directly or indirectly to generate colored products, which can then be detected optically, are suited for use in the subject system. Exemplary reactants include but are not limited to one or more enzymes, co-factors, dyes, and other reagents as needed to convert these and analytes to a colored product.

Of particular interest are several color forming reactants for use in the present invention. In one embodiment, peroxidase reactions are preferably used to generate colored products. Peroxidase chromogens are well known in the art, as exemplified by Trinder reagents such as TODB or TOOS (N-ethyl-N-(2-hydroxy-3-sulfopropyl)-3-methylaniline, sodium salt, dehydrate) used in combination with 4-aminoantipyrene, triaryl imidazoles, and ABTS (2,2'-azino-bis (3-ethylbenzthiazoline-6-sulfonic acid). In the chemistry of peroxidase reactions with Trinder reagents, two colorless organic molecules form a colored product in the presence of peroxidase and hydrogen peroxide. This peroxidase chemistry advantageously generates an intensely colored product and is not subject to interference from substances in blood plasma.

Reactants in the assay assembly can be contained in reaction sites, either as fluids or dry reagents. In the case of dry reagents, the reaction site preferably forms a rigid support on which a reactant can be immobilized. The reaction site surface is also chosen to provide characteristics for detection of light absorbance. For instance, the reaction site may be functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polypropylene, or combinations thereof. Other appropriate materials may be used in accordance with the present invention.

One skilled in the art will appreciate that there are many ways of immobilizing various reactants onto a support where reaction can take place. The immobilization may be covalent or noncovalent, via a linker moiety, or tethering them to an immobilized moiety. These methods are well known in the field of solid phase synthesis and micro-arrays (Beier et al., Nucleic Acids Res. 27:1970-1-977 (1999). Non-limiting exemplary binding moieties for attaching either nucleic acids or proteinaceous molecules such as antibodies to a solid support include streptavidin or avidin/biotin linkages, carbamate linkages, ester linkages, amide, thiolester, (N)-functionalized thiourea, functionalized maleimide, amino, disulfide, amide, hydrazone linkages, and among others. In addition, a silyl moiety can be attached to a nucleic acid directly to a substrate such as glass using methods known in the art.

In a preferred embodiment, there are multiple reaction sites in an assay assembly which can allow for detection of multiple analytes of interest from the same sample of bodily fluid. In some embodiments there are 2, 3, 4, 5, 6, or more reaction sites, or any other number of reaction sites as may be necessary to carry out the intent of the invention.

In embodiments with multiple reaction sites in a fluidic device, each reaction site may be immobilized with reactants different from reactants immobilized at a different reaction site. In a fluidic device with, for example, three reaction sites, there may be three different reactants, each immobilized to a different reaction site to detect three different analytes of interest in the sample.

In some embodiments, the reactants are contained in a reactant chamber. A reactant chamber is preferably in fluid communication with at least one reaction site, and when the fluidic device is actuated, reactants contained in the reactant chamber are released into a fluidic channel within the fluidic device and introduced into a reaction site. Reactants may be contained in reactant chambers as fluids or dry reagents, as described above with respect to reactants contained in reaction sites. In some embodiments there may be two, three, four, five, six, or more, or any number of reactant chambers as are necessary to fulfill the purposes of the invention.

In addition to color-forming reactants, the present invention may include other reagents. Such reagents can be stored with reactants in reaction sites or reactant chambers, if appropriate. In another embodiment reagents are stored separately, and there is at least one reagent chamber. Reagents may be stored in a fluid or dry state, similar to reactants. In some embodiments there may be two, three, four, five, six, or more, or any number of reagent chambers as are necessary to fulfill the purposes of the invention. A reagent chamber is preferably in fluid communication with at least one reaction site, and when the fluidic device is actuated, reagents contained in said reagent chambers are released into the fluidic channels within the fluidic device and introducted into a reaction site.

Reagents according to the present invention include without limitation wash buffers, enzyme substrates, dilution buffers, conjugates, enzyme-labeled conjugates, DNA amplifiers, sample diluents, wash solutions, sample pretreatment reagents including additives such as detergents, polymers, chelating agents, albumin-binding reagents, enzyme inhibitors, enzymes, anticoagulants, red-cell agglutinating agents, antibodies, or other materials necessary to run an assay in a fluidic device. In general, reagents especially those that are relatively unstable when mixed with liquid are confined in a defined region (e.g. a reagent chamber) within the subject fluidic device. The containment of reagents can be effected by valves that are normally closed and designed for one-time opening, preferably in a unidirectional manner. In some embodiments the reagents are initially stored dry and liquified upon initiation of the assay being run on the fluidic device.

In some embodiments a reactant site, reactant chamber or reagent chamber contains approximately about 50 μl to about 1 ml of fluid. In some embodiments the chamber may contain about 100 μl of fluid. The volume of liquid in a reactant or reagent chamber may vary depending on the type of assay being run or the sample of bodily fluid provided.

In preferred embodiments of the invention the fluidic device includes at least one waste chamber to trap or capture all liquids after they have been used in the assay. In preferred embodiments, there is more than one waste chamber, at least one of which is to be used with a calibration assembly described herein below. On-board waste chambers also allow the device to be easily disposable. The waste chamber is preferably in fluidic communication with at least one reaction site.

Light Source

A colored product of an analyte-detecting assay of the present invention is typically detected by measurement of absorbance of light by the colored product. Light will be directed to the colored product in a reaction site from a source that emits a spectrum of light in which at least one wavelength of light corresponds to the absorption spectrum of the colored product. The spectrum of the light emitted by a source accordingly will be similar to the spectrum of the absorbing species in the colored product of the analyte-detecting reaction. Preferably, the emission spectrum from the light source will overlap the absorption spectrum of the absorbing species, preferably by at least about 50%, 60%, 70%, 80%, 90% or 95%. However, the present invention does not require an exact overlap between the light source emission spectrum and the absorption spectrum of the colored product, as described in the examples provided herein. Use of monochromatic light sources and/or filters can generally provide a means to match the characteristics of the absorption and the light source.

The colored products detected by the subject system typically have an absorption range of about 250 nm to about 900 nm. Preferably, the color to be measured is generally in a visible range of about 400 to about 800 nm.

The absorbance of the colored product can be readily detected and in a range that is preferably stoichiometrically or linearly corresponds to the amount of analyte present. According to Beer's law, absorbance=concentration×extinction coefficient×optical path length. Chromophores in the visible wavelength range and typically used in clinical chemistry have extinction coefficients in the range of about $10^3$-$10^5$ L/(mole×cm). As shown in Table 1 of Example 1, a concentration of 1.5 mM analyte, diluted by 1:30 fold, gives an absorbance of 0.25 (44% transmission) when measured at the maximum absorbance (at λmax of 500 nm, the extinction coefficient=50,000 L/(mole×cm) with a path length of 0.1 cm (typical of single use cartridges). This absorbance is readily measurable by simple transmission optical systems.

A variety of light sources may be utilized for the present invention depending on the particular type of application and absorbance spectrum requirements for a given analyte of interest. An example of an appropriate light source includes, but is not limited to, an incandescent bulb, a light emitting diode, luminescent paint, and a laser. Preferably, the light source is an economical, low intensity light source well suited for point-of-care testing. When coupled with a photomultiplier tube detector, the number of photons generated by the light source need only be a few thousand over a measurement interval, which can range from a few milliseconds to a several minutes.

One type of light source applicable for the present invention is luminescent paint. Such paint is generally formulated using very tiny quantities of a long-lived radioisotope together with a material that glows or scintillates non-destructively when irradiated. The paint can be appropriately colored by addition of dyes. The paint will generally be coated on the non-transparent walls of a reaction site where analyte assay chemistry generates a colored product. Light emitted from the paint can be detected through a transparent surface of the reaction site to allow measurement of absorbance due to a colored product. The spectrum of the light emitted will generally be a function of the scintillant material and the absorbance characteristics of the chemistry used in forming a colored product.

Another applicable light source for the present invention is a Light Emitting Diode (LED). A LED can provide colored light at moderate intensity. The spectrum of the emitted light can be selected over the visible range. A LED typically has a more narrow range of emission wavelengths of about 30 nm. Thus, use of a LED as a light source will depend on the absorbance spectrum of an absorbing species used in the detection of a particular analyte.

Detector

Detection and measurement of colored products generated due to the presence of a given analyte can be made directly from a reaction site or alternatively from a detection site to which the colored product is transported. Preferably, detection will be made from a reaction site. Unless specified otherwise, the term "reaction site" as used herein will refer to both the site at which a reaction occurs and at which the colored product of the reaction is detected. The reaction site will typically be a well that is cylindrical in shape having a defined length between two opposed flat surfaces for determination of absorbance. For example, the point-of-care fluidic devices of the present invention might have a reaction site that is 0.1 cm in length. At least one or both of the flat surfaces of the reaction site will be transparent to allow detection of the colored product with standard transmission optics. The non-transparent surfaces of the reaction site may be made of opaque, white light scattering material.

The detector of light transmitted from a light source through a reaction site will be capable of detecting absorbance of light by the colored product in the reaction site. Examples of suitable detectors include, but are not limited to, a photomultiplier tube, a photodiode or an avalanche photodiode.

In a system of the present invention, the position of the light detector in the system relative to the fluidic device will depend on factors such as the type of light source used and the relative position of the light source to the fluidic device. In the case where the light source is a luminescent paint contained within a reaction site of the device, the detector will be positioned to detect light emitted from a transparent surface of the reaction site.

In the situation where the light source is external to a fluidic device, a detector could be positioned either on the same side or an opposite side of the fluidic device relative to the light source. A reaction site can be configured with a single transparent surface, through which light is both directed to the reaction and detected from the reaction. In this scenario, a detector is positioned on the same side of the fluidic device as the light source, with the detector shielded such that the only light detected is that from the reaction site of the fluidic device. Alternatively, a reaction site can be configured with two flat, opposed transparent surfaces such that the reaction site is effectively an optical cuvette. In this configuration, the light source would emit light to one side of the reaction site in the fluidic device and the detector would detect the light transmitted through the colored product to the opposite side of the reaction site in the fluidic device.

The fluidic devices of the present invention preferably function as handheld devices in a point-of-care system. The term "handheld" refers to a device that is both small and light enough to be easily held in an adult's hand, and can readily be placed by hand into operation within a point-of-care system. A handheld device of the present invention may assume a variety of overall configurations, such as rectangular, triangular, circular, oval and so forth. Regardless of the overall configuration, a handheld device of the present invention may typically be enclosed within rectangular dimensions of about 30×30×15 cm (length×width×height), or about 12×10×5 cm, or about 8×6×1.5 cm, and even smaller, such as about 7×5×1 cm.

A "point-of-care" system as used herein refers to a system that may be used at a patient's home, bedside, or other environment for performing any type of bodily fluid analysis or test outside of a central laboratory. A point-of-care system of the present invention will enable testing to be efficiently carried out by a patient or an assistant, a health care provider, and so forth. A point-of-care system preferably has dimensions and a configuration that allows it to be conveniently transported to a user's desired environment and readily used for testing.

Figure 1:
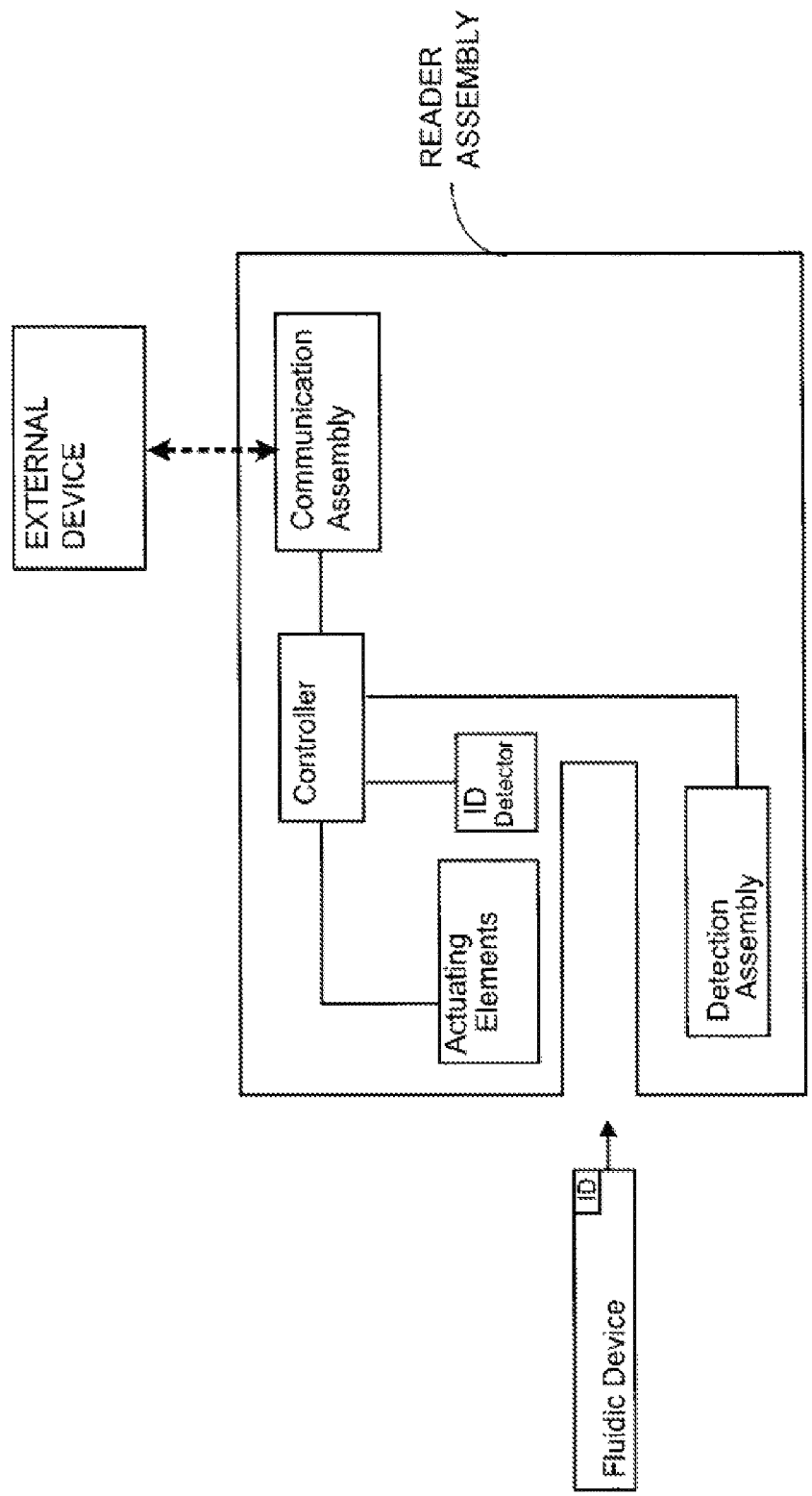
FIG. 1 depicts an exemplary point-of-care system of the present invention.

FIG. 1 illustrates an exemplary system of the present invention. As illustrated, a fluidic device provides a bodily fluid from a patient and can be inserted into a reader assembly. The fluidic device may take a variety of configurations and in some embodiments the fluidic device may be in the form of a cartridge. An identifier (ID) detector may detect an identifier on the fluidic device. The identifier detector communicates with a communication assembly via a controller which transmits the identifier to an external device. Where desired, the external device sends a protocol stored on the external device to the communication assembly based on the identifier. The protocol to be run on the fluidic device may comprise instructions to the controller of the reader assembly to perform the protocol on the fluidic device, including but not limited to a particular assay to be run and a detection method to be performed. Once the assay is performed on the fluidic device, a signal indicative of an analyte in the bodily fluid sample is generated and detected by a detector. The detected signal may then be communicated to the communications assembly, where it can be transmitted to the external device for processing, including without limitation, calculation of the analyte concentration in the sample.

Figure 2:
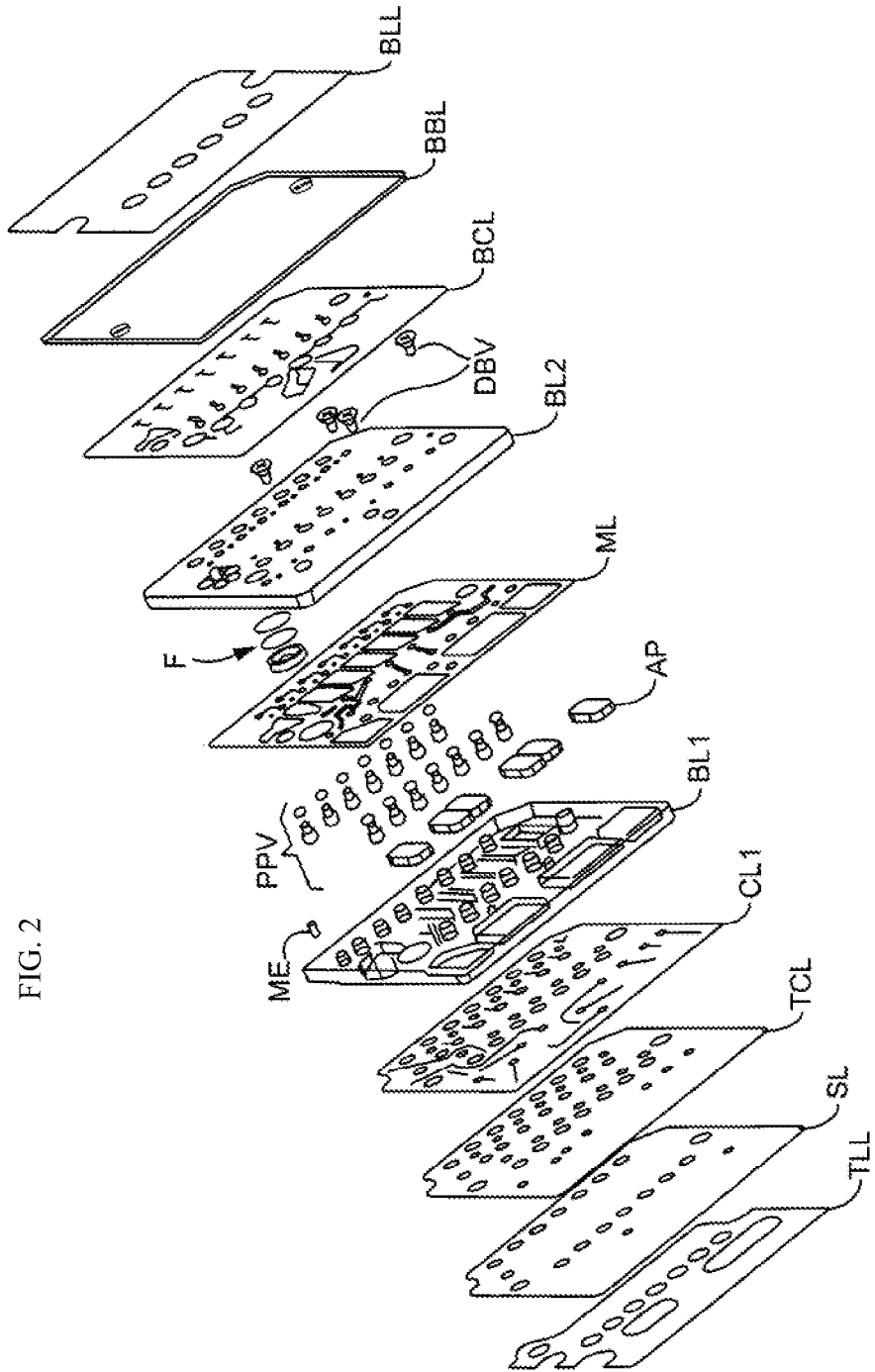
FIG. 2 shows a perspective view of various layers of an exemplary fluidic device of the present invention.
Figure 3:
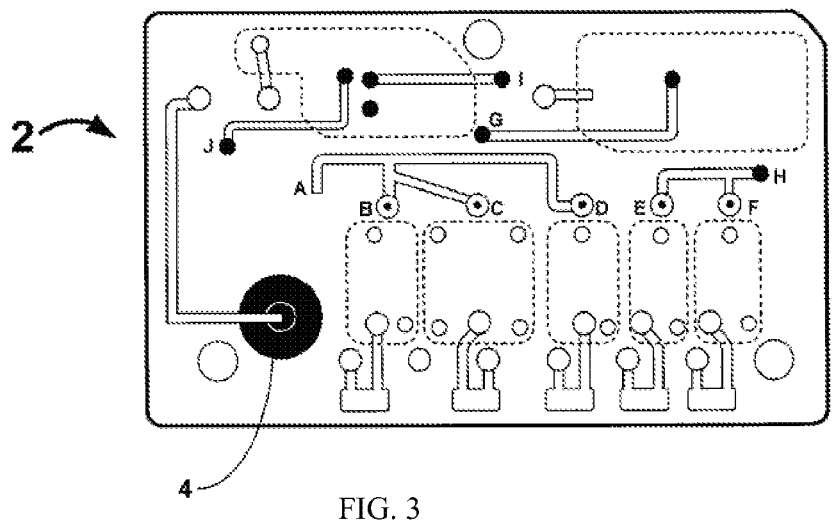
FIGS. 3 and 4 illustrate the fluidic network within an exemplary fluidic device.
Figure 4:
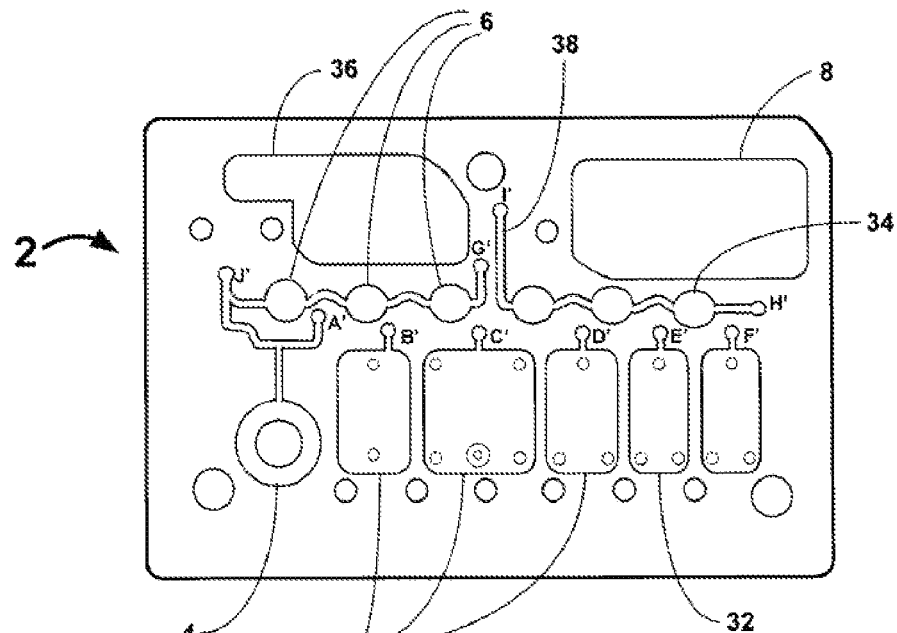

FIG. 2 illustrates exemplary layers of a fluidic device according to the present invention prior to assembly of the fluidic device. FIGS. 3 and 4 show a top and bottom view, respectively, of an exemplary fluidic device after the device has been assembled. The different layers are designed and assembled to form a three dimensional fluidic channel network. A sample collection unit provides a sample of bodily fluid from a patient. A reader assembly comprises actuating elements (not shown) that can actuate the fluidic device to start and direct the flow of a bodily fluid sample and assay reagents in the fluidic device. In some embodiments actuating elements first cause the flow of sample in the fluidic device from a sample collection unit 4 to reaction sites 6, and then to waste chamber 8 following completion of reactions in the sites. If necessary for a given reaction, the actuating elements initiate flow of reagents from reagent chambers 10 to reaction sites, and then to waste chamber 8 in a manner similar to that of the sample.

A fluidic device of the present system can run a variety of assays, regardless of the analyte being detected from a bodily fluid sample. A protocol dependent on the identity of the fluidic device may be transferred from an external device where it can be stored to a reader assembly to enable the reader assembly to carry out the specific protocol on the fluidic device. In preferred embodiments, the fluidic device has an identifier (ID) that is detected or read by an identifier detector. The identifier can then be communicated to a communication assembly, where it can then be transferred or transmitted to an external device.

In one embodiment, a bodily fluid sample is provided to a fluidic device, which is then inserted into a reader assembly. In some embodiments the fluidic device is partially inserted manually, and then a mechanical switch in the reader assembly automatically properly positions the fluidic device inside the reader assembly. Any other mechanism known in the art for inserting a disk or cartridge into a device may be used as well. In some embodiments only manual insertion may be required.

In preferred embodiments the reader assembly houses a controller which controls a pump and a series of valves to control and direct the flow of liquid within the fluidic device. In some embodiments the reader assembly may comprises multiple pumps. The sample and reagents are preferably pulled through the fluidic channels by a vacuum force created by sequentially opening and closing at least one valve while activating a pump within the reader assembly. Methods of using at least one valve and at least one pump to create a vacuum force are well known. While a negative pulling force may be used, a positive pushing force may also be generated by at least one pump and valve according to the present invention. In other embodiments movement of fluid on the fluidic device may be by electro-osmotic, capillary, piezoelectric, or microactuator action.

One of the advantages of the present invention is that any reagents necessary to perform an assay on a fluidic device according to the present invention are preferably on-board, or housed within the fluidic device before, during, and after the assay. In this way the only inlet or outlet from the fluidic device is preferably the bodily fluid sample initially provided by the fluidic device. This design also helps create an easily disposable fluidic device where all fluids or liquids remain in the device. The on-board design also prevents leakage from the fluidic device into the reader assembly which should remain free from contamination from the fluidic device.

Method of Use

The subject apparatus and systems provide an effective means for high throughput and/or real-time detection of analytes present in a bodily fluid from a subject. The detection methods may be used in a wide variety of circumstances including identification and quantification of analytes that are associated with specific biological processes, physiological conditions, disorders or stages of disorders. As such, the subject apparatus and systems have a broad spectrum of utility in, e.g. drug screening, disease diagnosis, phylogenetic classification, parental and forensic identification. The subject apparatus and systems are also particularly useful for advancing preclinical and clinical stage development of therapeutics, improving patient compliance, monitoring adverse drug responses associated with a prescribed drug, and developing individualized medicine.

Accordingly, in one embodiment, the present invention provides a method of detecting an analyte in a bodily fluid from a subject. The method typically involves the steps of (a) introducing a sample of bodily fluid into a fluidic device having a sample collection unit and an assay assembly, the assay assembly having reactants that are capable of reacting with an analyte; (b) allowing the sample of bodily fluid to react with the reactants contained within the assay assembly to yield a colored product having an absorbance spectrum corresponding to at least one wavelength from a light source; (c) transmitting light having the at least one wavelength to the fluidic device from the light source; and (d) detecting absorption of light of the at least one wavelength transmitted to the fluidic device, wherein the absorption is indicative of the presence of the analyte in said bodily fluid.

Any bodily fluids suspected to contain an analyte of interest can be used in conjunction with the subject methods of detection. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid. The volume of bodily fluid to be used in methods of the present invention is generally less than about 500 microliters, and preferably less than about 50 microliters. Where desired, a sample of 1 to 50 microliters, 1 to 40 microliters, 1 to 30 microliters, 1 to 20 microliters, or 1 to 10 microliters can be used for detecting an analyte using the subject fluidic device.

A bodily fluid may be drawn from a patient and brought into the fluidic device in a variety of ways, including but not limited to, lancing, injection, or pipetting. In one embodiment, a lancet punctures the skin and draws the sample into the fluidic device using, for example, gravity, capillary action, aspiration, or vacuum force. The lancet may be part of the fluidic device, or part of a reader assembly, or as a stand alone component. Where needed, the lancet may be activated by a variety of mechanical, electrical, electromechanical, or any other known activation mechanism or any combination of such methods. In another embodiment where no active mechanism is required, a patient can simply provide a bodily fluid to the fluidic device, as for example, could occur with a saliva sample. The collected fluid can be placed in the sample collection unit within the fluidic device. In yet another embodiment, the fluidic device comprises at least one microneedle which punctures the skin. The microneedle can be used with a fluidic device alone, or can puncture the skin after the fluidic device is inserted into a reader assembly.

In some embodiments a microneedle is about the size of a human hair and has an integrated microreservoir or cuvette. The microneedle may painlessly penetrate the skin and draw a small blood sample. More preferably, the microneedle collects about 0.01 to about 1 microliter, preferably about 0.05 to about 0.5 microliters and more preferably about 0.1 to about 0.3 microliters of capillary blood. In some embodiments a microneedle may be constructed out of silicon and is about 10 to about 200 microns in diameter, preferably about 50 to about 150 microns in diameter, and most preferably about 100 microns in diameter, making their application to the skin virtually painless. To ensure that a capillary is actually struck by a needle, a plurality of microneedles may be used for sample collection. Such microneedles may be of the type marketed by Pelikan (Palo Alto, Calif.) and/or Kumetrix (Union City, Calif.). U.S. Pat. No. 6,503,231 discloses microneedles which may be used with the present invention.

In preferred embodiments a microneedle is only used once and then discarded. In some embodiments a mechanical actuator can insert and withdraw the microneedle from the patient, discard the used needle, and reload a new microneedle.

In some embodiments the method of detecting an analyte in a bodily fluid from a subject includes metering a predetermined portion of the sample, in which this predetermined portion is assayed for the presence of analytes. The volume of the predetermined portion will preferably be less than about 500 microliters, more preferably about less than 50 microliters, or even more preferably, the volume is about 10 microliters.

A precise sample volume is determined by several features. In one embodiment a subject places a sample of bodily fluid into the sample collection well, after which the sample is drawn into a metering channel by capillary action until it reaches a stop junction at the entrance of the mixing chamber. The metering channel preferably has physical dimensions and surface characteristics which reliably promote flow of blood from the sample collection well.

In a preferred embodiment, a predetermined portion of a sample is diluted and mixed with a diluent to yield a diluted sample, which is then assayed for the presence of analytes. A predetermined portion is diluted with a diluent that is typically contained in a diluent chamber, with the portion and diluent being mixed in a mixing chamber. Preferably, the diluent is flowed into the metering channel, which flushes the sample into the mixing chamber. A precise volume of diluent is stored in the dilution chamber. A precise volume of diluent, a precise volume of the predetermined portion of a sample, and efficient combination and mixing of the two volumes allows the sample to be diluted with a high degree of precision.

In some embodiments, the fluid sample will be filtered before entering a reaction chamber. For example, blood may be filtered to remove red blood cells. Where a sample is diluted before assaying, filtering will typically occur after dilution. Filtering will occur in a filter chamber, through which the sample is transported before entering into a reaction site.

A variety of assays may be performed on a fluidic device according to the present invention to detect an analyte of interest in a sample. Analytes that may be detected by the subject methods include, but are not limited to, drugs, drug metabolites, biomarkers indicative of disease, tissue specific markers, tissue specific enzymes, hormones, antibodies, pathogens, HDL cholesterol, LDL cholesterol, total cholesterol, lipids, and glucose.

The subject methods involve reactants that are capable of reacting with an analyte of interest to generate a color product for detection by optical means. The choice of reactants will depend on the particular analyte being examined.

For detection of levels of total cholesterol (i.e., the sum of free and esterified cholesterol) in a bodily fluid, reactants including cholesterol esterase, cholesterol oxidase, an oxidizable dye such as n,n-bis(4-sulfobutyl)-3-methylaniline, disodium salt (TODB), 4-aminoantipyrine, and horse radish peroxidase can be employed. In this reaction scheme, cholesterol esterase converts esterified cholesterol to free cholesterol. Cholesterol oxidase transforms the free cholesterol into cholest-4-ene-3-one and hydrogen peroxide. The amount of hydrogen peroxide generated can be quantified by a spectrophotometric assay, for example the oxidative coupling of 4-aminoantipyrine and TODB in the presence of peroxidase to form a chromophore. The amount of chromophore formed is then measured by light attenuation (absorbance), which corresponds to the amount of total cholesterol.

Measuring the ALT levels as a way for assaying liver function can be carried out by reacting the analyte from a bodily fluid with reactants such as alphaketoglutarate, pyruvate oxidase, an oxidizable dye such as N,N-Bis(4-sulfobutyl)-3-methylaniline, disodium salt (TODB), 4-aminoantipyrine, and horse radish peroxidase. In this assay reaction scheme, ALT catalyzes the transfer of amino groups from L-alanine to alphaketoglutarate, producing pyruvate and glutamate. Pyruvate oxidase oxidizes the pyruvate to acetylphosphate and hydrogen peroxide. Horseradish peroxidase catalyzes the reaction of the peroxide reacts with TODB to form a colored product at a rate proportional to the ALT concentration of the sample. The resultant colored product in the reaction is measured by light absorbance.

The methods of the present invention can also be used to detect analytes, such as small molecule drugs, biomarkers, hormones, and antibodies, through binding of an agent that then participates in a color-producing reaction. For example, an analyte can be detected through binding and color formation that occurs in immunoassays, such as an enzyme-linked immunosorbent assay (ELISA). In a typical ELISA, an analyte is specifically bound by an antibody, which in turn is detected by a secondary, enzyme-linked antibody. The linked enzyme catalyzes a color-producing reaction. Enzymes such as β-galactosidase, alkaline phophatase and horse radish peroxidase are often utilized for color formation in ELISAs. The light absorbance of colored products generated in an ELISA is typically in a range well suited for the present invention. Reactants of the present invention accordingly will include reagents for an ELISA or similar immunoassay. Unlike typical assays for detection of analytes that are chemical reactants or promote a chemical reaction, ELISA immunoassays require wash steps, and thus generally will occur in separate, dedicated reaction sites.

A colored product will be detected in methods of the present invention through measurement of absorbance of light by the colored product. The light to be transmitted in the methods of the present invention will be from a source that emits a spectrum of light in which at least one wavelength of light corresponds to the absorption spectrum of the colored product. The range of absorption spectra of colored products will correspond to a wavelength range of about 250 nm to about 900 nm. Preferably, the color to be measured is generally in a visible range of about 400 to about 800 nm. The spectrum of light emitted by a source accordingly will be similar to the absorption spectrum of the colored product. Preferably, the emission spectrum from a light source will exactly overlap the absorption spectrum of the absorbing species. However, an exact overlap between the light source emission spectrum and the absorption spectrum of the colored product is not required for measurement by the methods of the present invention, as described in the examples provided herein. Monochromatic light sources and/or filters generally can be used to provide a means to match the characteristics of the absorption and the light source.

A variety of light sources may be utilized for the present invention depending on the particular type of application and absorbance spectrum requirements for a given analyte of interest. An example of an appropriate light source includes, but is not limited to, an incandescent bulb, a light emitting diode, luminescent paint, and a laser.

The position of the light source relative to the reaction site will depend on the particular source of light. Typically, a light source will transmit light into the reaction site through a transparent, flat surface of the reaction site. In this scenario, the light source will be external to the fluidic device, with the reaction site aligned with the light source so that light is transmitted directly into the reaction site. To enable measurement from several reaction sites, the fluidic device and light source will be moveable relative to each other to allow alignment of more than one individual reaction site with the light source. Either the fluidic device, light source, or a combination of the two can be moveable within a system to allow alignment.

As an alternative to light being transmitted into the reaction site from an external source, the methods of the present invention can utilize a luminescent paint as an internal light source. In this scenario, the luminescent paint will emit light through a colored product contained in the reaction site. For example, the reaction site could have a cylindrical shape, with two flat opposed surfaces, with one being transparent, the other being coated with a luminescent paint. The luminescent paint will emit light through the colored product, which could be detected by a detector as detailed below. Luminescent paint is generally formulated using very tiny quantities of a long-lived radioisotope together with a material that glows or scintillates non-destructively when irradiated. The paint can be appropriately colored by addition of dyes. The spectrum of light emitted will generally be a function of the scintillant material and the absorbance characteristics of the chemistry used in forming a colored product.

The light generated in the methods of the present invention will be detected by a detector that will be external to the fluidic device. Examples of suitable detectors include, but are not limited to, a photomultiplier tube, a photodiode or an avalanche photodiode.

The position of the light detector relative to the fluidic device will depend on the light source used and its relative position to the fluidic device. In the case where the light source is a luminescent paint contained within a reaction site of the device, the detector can be positioned as necessary to be aligned with a transparent surface of the reaction site to detect light emitted through a colored product.

In the situation where the light source is external to a fluidic device, a detector could be positioned either on the same side or an opposite side of the fluidic device relative to the light source. A reaction site can be configured with a single transparent surface to allow both light transmission into the site and detection from the site. In this scenario, a detector would be positioned on the same side of the fluidic device as the light source, and shielded such that the only light detected is that emitted from the reaction site of the fluidic device. Alternatively, a reaction site can be configured with two flat, opposed transparent surfaces such that the reaction site is effectively an optical cuvette. In this configuration, the light source would transmit light to one side of the reaction site in the fluidic device and the detector would detect the light transmitted through the colored product to the opposite side of the reaction site in the fluidic device. In either scenario, the detector will be positioned to align with the reaction site to detect light emission.

To allow measurement from several reaction sites, the fluidic device and light detector will be moveable relative to each other to allow alignment of more than one individual reaction site with the light detector. Either the fluidic device, the detector, or a combination of the two can be moveable to allow alignment.

In addition to detection of the presence of an analyte in a bodily fluid, the methods of the present invention also provide for quantitation of the concentration of an analyte in a bodily fluid through measurement of absorbance. Concentration of the analyte is related to the amount of light adsorbed by the colored product. In the case of analytes that can be converted directly or indirectly into colored product, such as cholesterol, the conversion to product is typically stoichiometric. For instance, the amount of color produced can linearly increase with the amount of analyte present. The corresponding absorbance can be proportionately related to the amount of color produced, and therefore the concentration of analyte present. However, at high concentrations, the proportionality of absorbance to concentration set forth by Beer's Law does not necessarily hold. Thus, an accurate measurement of analyte present at high concentration may depend on an appropriate dilution of a bodily fluid, the characteristics of the particular absorbing species, and the length of cell path from which determination of absorbance is made.

Analytes that are detected by their ability to catalyze formation of a colored product, such as the enzyme ALT, can be quantified following a particular length of reaction time. By allowing an analyte enzyme to react for a fixed period of time, appropriate quantities of measurable, colored product can be generated. For example, a fixed period of time under conditions in which the amount of an analyte enzyme is a rate-limiting factor can give rise to uM-nM quantities of colored product. The quantity of product generated can be measured at the end of the time period by measurement of light attenuation and determination of absorbance. The amount of analyte can then be determined based on the amount of product generated over time, based on known kinetics of a given analyte under the conditions of a particular assay used. An accurate measurement of analyte will depend on the particular analyte being examined, conditions under which it is assayed (at what dilution, temperature, and so on), the characteristics of the particular absorbing species, and the length of cell path from which determination of absorbance is made.

In some embodiments immunoassays are run on the fluidic device. While competitive binding assays, which are well known in the art, may be run in some embodiments, in preferred embodiments a two-step method is used which eliminates the need to mix a conjugate and a sample before exposing the mixture to an antibody, which may be desirable when very small volumes of sample and conjugate are used, as in the fluidic device of the present invention. A two-step assay has additional advantages over the competitive binding assays when use with a fluidic device as described herein. It combines the ease of use and high sensitivity of a sandwich (competitive binding) immunoassay with the ability to assay small molecules.

In an exemplary two-step assay, the sample containing analyte first flows over a reaction site containing antibodies. The antibodies bind the analyte present in the sample. After the sample passes over the surface, a solution with analyte conjugated to a marker at a high concentration is passed over the surface. The conjugate saturates any of the antibodies that have not yet bound the analyte. Before equilibrium is reached and any displacement of pre-bound unlabelled analyte occurs, the high-concentration conjugate solution is washed off. The amount of conjugate bound to the surface is then measured by the appropriate technique, and the detected conjugate is inversely proportional to the amount of analyte present in the sample.

The methods of the present invention provide for monitoring more than one pharmacological parameter useful for assessing efficacy and/or toxicity of a therapeutic agent. For the purposes of this invention, a "therapeutic agent" is intended to include any substances that have therapeutic utility and/or potential. Such substances include but are not limited to biological or chemical compounds such as simple or complex organic or inorganic molecules, peptides, proteins, or polynucleotides. A vast array of compounds can be synthesized, for example polymers, such as polypeptides and polynucleotides, and synthetic organic compounds based on various core structures, and these are also included in the term "therapeutic agent". In addition, various natural sources can provide compounds for screening, such as plant or animal extracts, and the like. It should be understood, although not always explicitly stated that the agent is used alone or in combination with another agent, having the same or different biological activity as the agents identified by the inventive screen. The agents and methods also are intended to be combined with other therapies.

Pharmacodynamic (PD) parameters according to the present invention include without limitation physical parameters such as temperature, heart rate/pulse, blood pressure, and respiratory rate, and biomarkers such as proteins, cells, and cell markers. Biomarkers could be indicative of disease or could be a result of the action of a drug. Pharmacokinetic (PK) parameters according to the present invention include without limitation drug and drug metabolite concentration. Identifying and quantifying the PK parameters in real time from a sample volume is extremely desirable for proper safety and efficacy of drugs. If the drug and metabolite concentrations are outside a desired range and/or unexpected metabolites are generated due to an unexpected reaction to the drug, immediate action may be necessary to ensure the safety of the patient. Similarly, if any of the pharmacodynamic (PD) parameters fall outside the desired range during a treatment regime, immediate action may have to be taken as well.

In preferred embodiments physical parameter data is stored in or compared to store profiles of physical parameter data in a bioinformatics system which may be on an external device incorporating pharmacogenomic and pharmacokinetic data into its models for the determination of toxicity and dosing. Not only does this generate data for clinical trials years prior to current processes but also enables the elimination of current disparities between apparent efficacy and actual toxicity of drugs through real-time continuous monitoring. During the go/no go decision process in clinical studies, large scale comparative population studies can be conducted with the data stored on the database. This compilation of data and real-time monitoring allows more patients to enter clinical trials in a safe fashion earlier than currently allowed. In another embodiment biomarkers discovered in human tissue studies can be targeted by the device for improved accuracy in determining drug pathways and efficacy in cancer studies.

Being able to monitoring the rate of change of an analyte concentration or PD or PK over a period of time in a single subject, or performing trend analysis on the concentration, PD, or PK, whether they are concentrations of drugs or their metabolites, can help prevent potentially dangerous situations. For example, if glucose were the analyte of interest, the concentration of glucose in a sample at a given time as well as the rate of change of the glucose concentration over a given period of time could be highly useful in predicting and avoiding, for example, hypoglycemic events. Such trend analysis has widespread beneficial implications in drug dosing regimen. When multiple drugs and their metabolites are concerned, the ability to spot a trend and take proactive measures is often desirable.

The present invention allows for automatic quantification of a pharmacological parameter of a patient as well as automatic comparison of the parameter with, for example, the patient's medical records which may include a history of the monitored parameter, or medical records of another group of subjects. Coupling real-time analyte monitoring with an external device which can store data as well as perform any type of data processing or algorithm, for example, provides a device that can assist with typical patient care which can include, for example, comparing current patient data with past patient data.

Where a statistically significant discrepancy exists between the detected values and the threshold value, a further action may be taken by a medical practitioner. Such action may involve a medical action such as adjusting dosage of the therapeutic agent; it may also involve a business decision such as continuing, modifying, or terminating the clinical trial.

One advantage of the current invention is that assay results can be substantially immediately communicated to any third party that may benefit from obtaining the results. For example, once the analyte concentration is determined at the external device, it can be transmitted to a patient or medical personnel who may need to take further action. The communication step to a third party can be performed wirelessly, and by transmitting the data to a third party's hand held device, the third party can be notified of the assay results virtually anytime and anywhere. Thus, in a time-sensitive scenario, a patient may be contacted immediately anywhere if urgent medical action may be required.

In some embodiments a patient may be provided with a plurality of fluidic devices to use to detect a variety of analytes. A subject may, for example, use different fluidic devices on different days of the week.

In some embodiments, the methods of the present invention are applicable for obtaining pharmacological data useful for assessing efficacy and/or toxicity of a pharmaceutical agent from a test animal. When using laboratory animals in preclinical testing of a pharmaceutical agent, it is often necessary to kill the test subject to extract enough blood to perform an assay to detect an analyte of interest. This has both financial and ethical implications, and as such it may be advantageous to be able to draw an amount of blood from a test animal such that the animal does not need to be killed. In addition, this can also allow the same test animal to be tested with multiple pharmaceutical agents at different times, thus allowing for a more effective preclinical trial. On average, the total blood volume in a mouse, for example, is 6-8 mL of blood per 100 gram of body weight. A benefit of the current invention is that only a very small volume of blood is required to perform preclinical trials on mice or other small laboratory animals. In some embodiment between about 1 microliter and about 50 microliters are drawn. In preferred embodiment between about 1 microliter and 10 microliters are drawn. In preferred embodiments about 5 microliters of blood are drawn.

A further advantage of keeping the test animal alive is evident in a preclinical time course study. When multiple mice, for example, are used to monitor the levels of an analyte in a test subject's bodily fluid over time, the added variable of using multiple subjects is introduced into the trial. When, however, a single test animal can be used as its own control over a course of time, a more accurate and beneficial preclinical trial can be performed.

In some embodiments the methods of the present invention can be used in methods of automatically monitoring patient compliance with a medical treatment. After determination of an analyte in a bodily fluid, the level of analyte can be compared with a known profile associated with the medical treatment to determine if the patient is compliant or noncompliant with the medical treatment; and notifying a patient of the compliance or noncompliance.

Noncompliance with a medical treatment, including a clinical trial, can seriously undermine the efficacy of the treatment or trial. As such, in some embodiments the system of the present invention can be used to monitor patient compliance and notify the patient or other medical personnel of such noncompliance. For example, a patient taking a pharmaceutical agent as part of medical treatment plan can take a bodily fluid sample which is assayed as described herein, but a detected metabolite concentration, for example, may be at an elevated level compared to a known profile thereby indicating multiple doses of the pharmaceutical agent have been taken. Such a known profile may be located or stored on an external device.

The following examples illustrate and explain the invention. The scope of the invention is not limited by these examples.

EXAMPLES

Example 1

Trinder Reagent Spectrum

Figure 8:
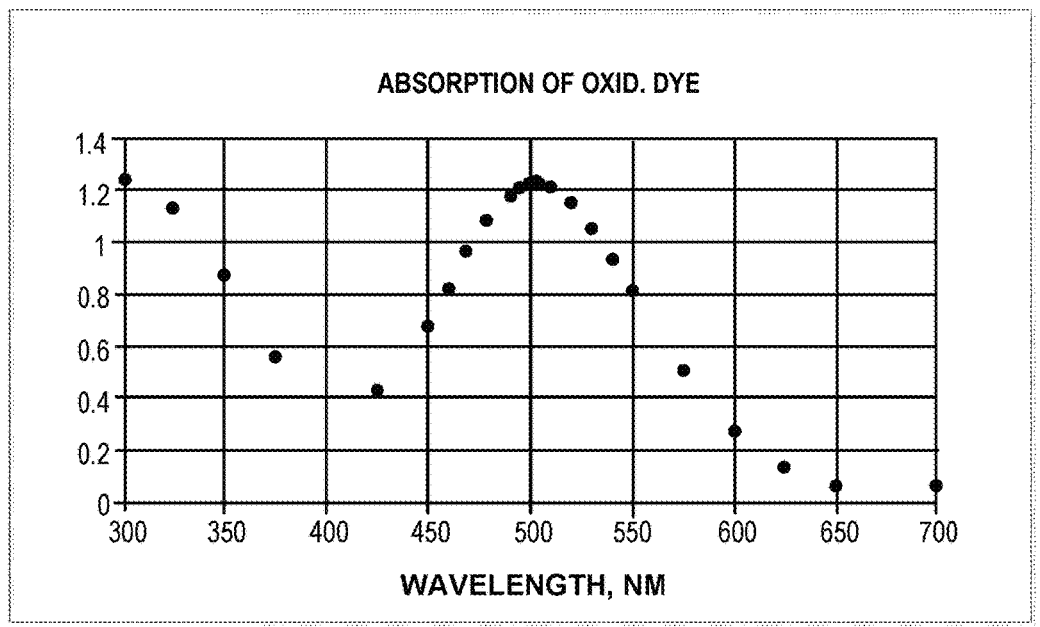
FIG. 8 shows an absorption spectrum of a Trinder product.

Several color forming chemistries are applicable for use in the present invention, including those of peroxidase reactions. Peroxidase chromophores are well known in the art, as exemplified by Trinder reagents such as TODB or TOOS. A Trinder reagent will generate a reaction product having an absorption spectrum such as that exemplified in FIG. 8. As shown in FIG. 8, the width of the absorption spectrum at about half height of spectrum is about 100 nm. The width of the spectrum indicates that the absorption characteristics of a Trinder reagent make measurement of absorption applicable over a range of wavelengths.

Example 2

Figure 9:
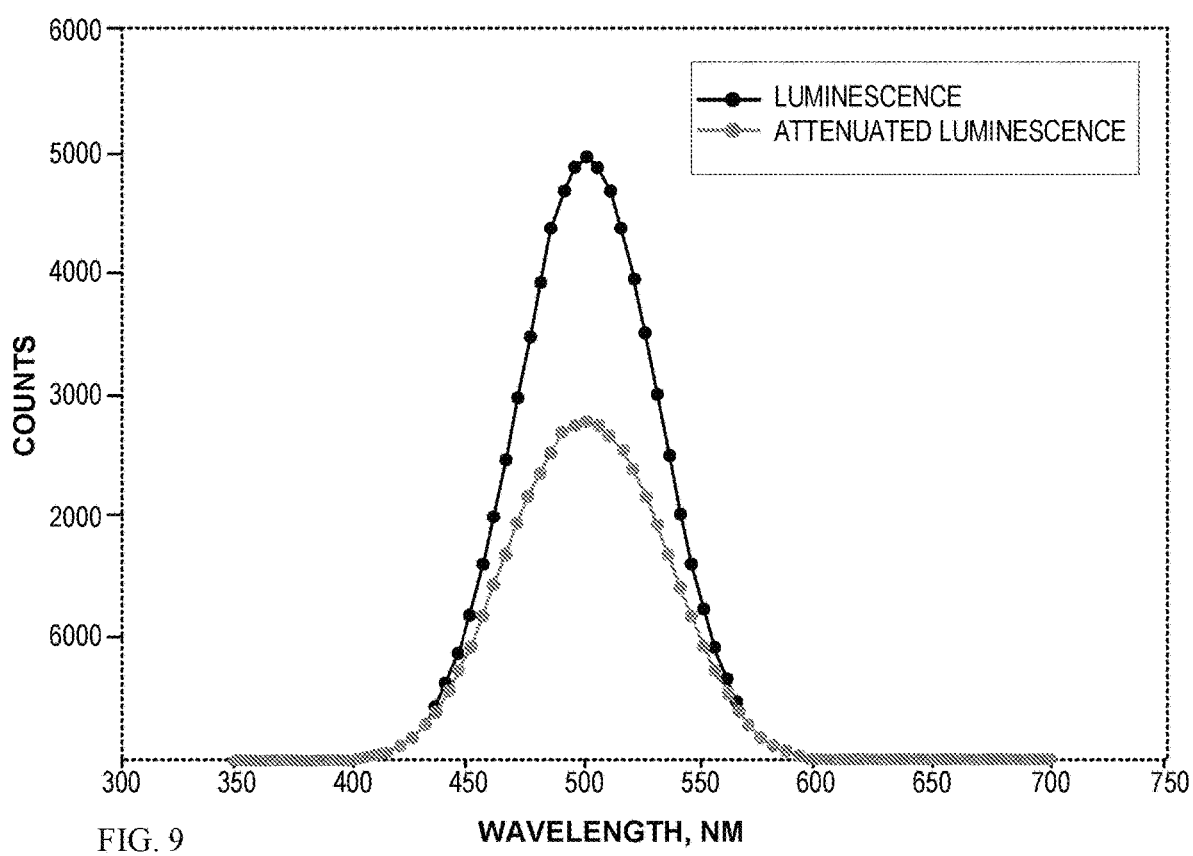
FIG. 9 shows the spectral response of an assay simulation using a light source having an emission spectrum that perfectly overlaps with an absorption spectrum of an absorbing species.

Assay Simulation for a Light Source and Absorbing Species Having Matching Spectrums In the present invention, a light source may have an emission spectrum that perfectly overlaps with the absorption spectrum of the absorbing species. Using values that are typical for the chemistry and devices of the present invention, Table 1 shows the calculation for one analyte concentration. As shown in Table 1, an analyte having a concentration of 1.5 mM gives an absorbance of 0.25 (44% transmission) after dilution 1:30 when measured at the maximum absorbance (at $\lambda max=50,000$) with a pathlength of 0.1 cm, which would be typical of single use cartridges. FIG. 9 demonstrates the spectral response at this concentration, from which it can be seen that the best response is at $\lambda max$ of 500 nm.

TABLE 1

Conditions for spectra

Luminescence

| | |
|---|---|
| λmax | 500 nm |
| Half width | 30 nm |
| Intensity | 100000 counts (total) |
| Absorption | |
| λmax | 500 nm |
| Half width | 40 nm |
| εM (λmax) | 50000 |
| Pathlength, 1 | 0.1 cm |
| Conc. (sample) | 1.50E−03M |
| Dilution | 30 Fold |
| A @ λmax | 2.50E−01 |
| ΔT@ λmax | 4.38E+01% |

Example 3

Cholesterol Assay

Figure 10:
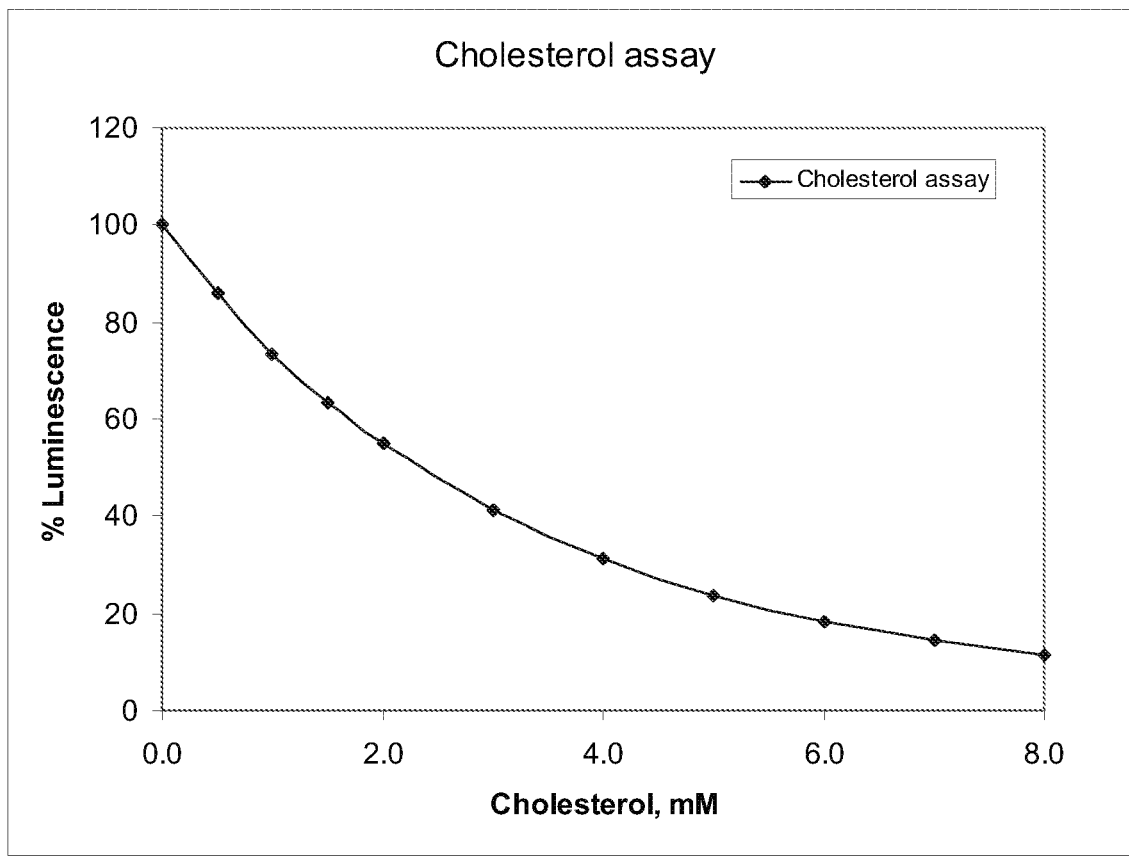
FIG. 10 shows a light attenuation response for a cholesterol assay.

Using the parameters given in Example 2, the response of a cholesterol assay is shown in FIG. 10 based on attenuation of light at λmax. As shown in FIG. 10, the assay signal measured at λmax is well modulated over the clinical range of tested cholesterol levels.

Example 4

Figure 11:
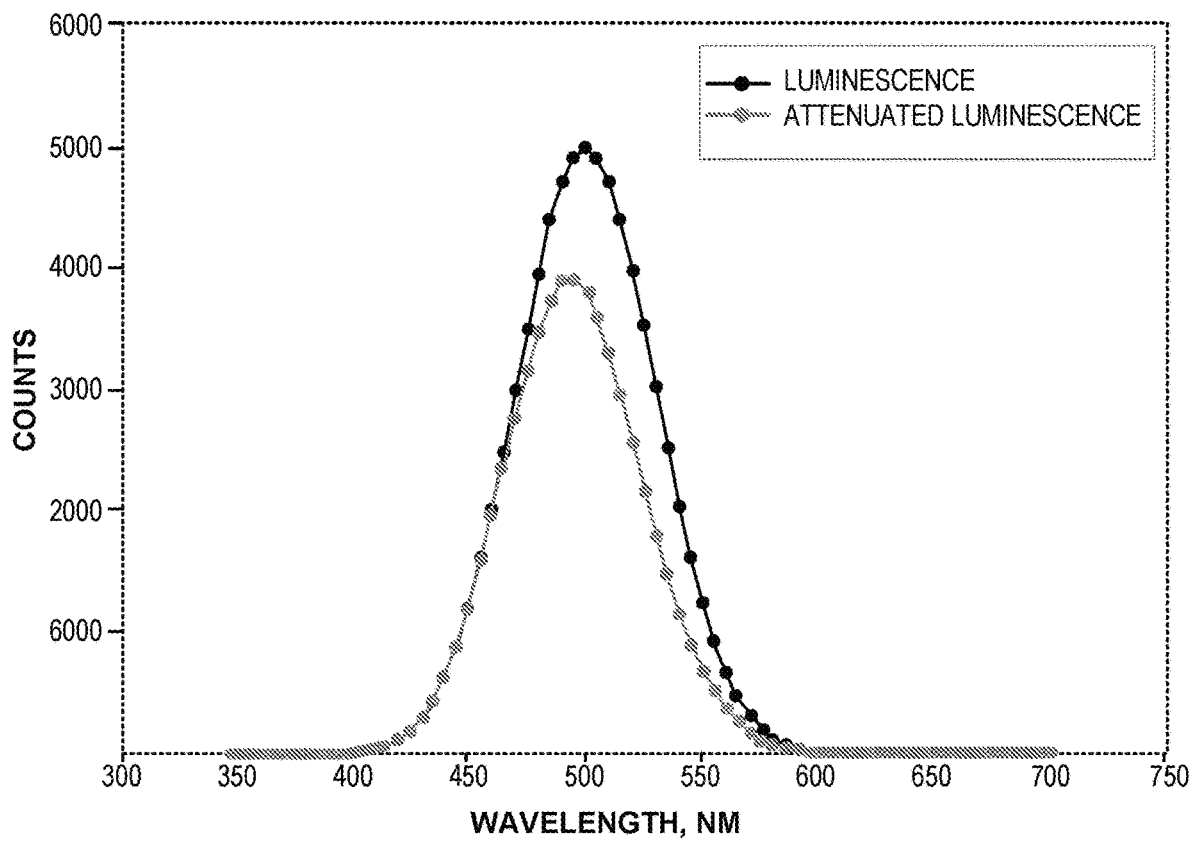
FIG. 11 shows simulation of the signal modulation for an assay in which a light emission spectrum and an absorption spectrum of the absorbing species overlaps, and the λmax varies between the two spectrums by 50 nm.

Assay Simulation for a Light Source and Absorbing Species Having Offset Spectrums In this example, the parameters are as given in Example 2, with the exception that there is a large offset between the spectrum of the light source and the absorption spectrum, with λmax being 50 nm higher for the absorption spectrum (550 nm rather than 500 nm). As seen in FIG. 11, the light attenuation at the λmax of emission (500 nm) is much less than for the ideal case, as shown in FIG. 9. At higher wavelengths, however, the fractional signal modulation between the two spectrums is improved, albeit at a lower signal level of absorption than that seen at λmax. While the light emission and absorption spectrums will preferably overlap exactly, the overlap need not be an exact match for utility in the present invention.

Example 5

Use of an Edge Filter to Improve Signal Modulation

Figure 12:
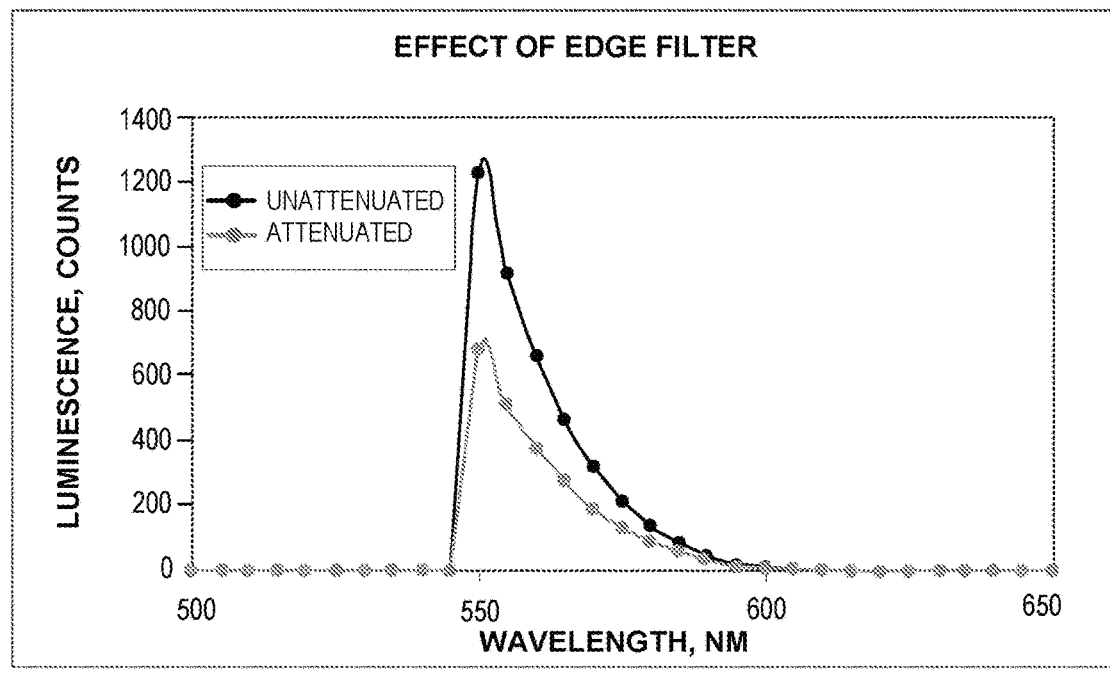
FIG. 12 shows simulation of the signal modulation for an assay in which a light emission spectrum and an absorption spectrum of the absorbing species overlaps, and the λmax varies between the two spectrums by 50 nm, where an edge filter with a cut-off below the lower λmax is used on either the emission or detection side of the optical system.

As shown in Example 4, overlap between light emission and absorption spectrums need not be an exact match for use in the present invention. However, monochromatic light sources and/or filters can generally be used to create a near exact match of the characteristics between a light source and the colored product absorption. Using the same parameters as used in Example 4, FIG. 12 demonstrates use of an edge filter with a cut-off of 490 nm used on either the light transmission or detection side of the optical system to improve signal modulation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A microfluidic cartridge for carrying out an assay to detect an analyte in a bodily fluid sample, comprising:
   a sample collection unit comprising a sample collection well for receiving the bodily fluid sample;
   an assay unit in fluid communication with the sample collection well, wherein the assay unit comprises a reactant chamber having a reaction site with a reactant immobilized on the reaction site and configured to react with the analyte in the bodily fluid sample to generate a colored product having an absorbance spectrum; and
   a light source comprising a luminescent paint coated on the reaction site, wherein a spectrum of light emitted from the luminescent paint has at least one wavelength that is a function of the absorbance spectrum.

2. The microfluidic cartridge of claim 1, wherein the sample collection unit further comprises a metering channel in fluid communication with the sample collection well, the metering channel configured to collect a predetermined portion of the bodily fluid sample to be assayed, wherein the assay unit is in fluid communication with the sample collection well by means of the metering channel, and wherein the predetermined portion of the bodily fluid sample has a volume of about 10 to about 50 microliters.

3. The microfluidic cartridge of claim 2, wherein the metering channel comprises a metering element configured to close off fluidic connection between the sample collection well and the metering channel to prevent a volume of the bodily fluid sample larger than the predetermined portion of the bodily fluid sample from being assayed.

4. The microfluidic cartridge of claim 3, wherein the metering element is a pin that is movable so as to close off fluidic connection between the sample collection well and the metering channel.

5. The microfluidic cartridge of claim 1, wherein the reactant chamber comprises a cylindrical configuration.

6. The microfluidic cartridge of claim 1, wherein the reactant chamber is at least partially transparent such that light can be transmitted through the reactant chamber.

7. The microfluidic cartridge of claim 6, wherein the reactant chamber comprises functionalized glass.

8. The microfluidic cartridge of claim 2, further comprising a dilution chamber in fluid communication with the metering channel of the sample collection unit, wherein the dilution chamber is configured to store a diluent.

9. The microfluidic cartridge of claim 1, further comprising a reagent chamber for storing a reagent for carrying out the assay to detect the analyte, wherein the reagent chamber is in fluid communication with the reactant chamber of the assay unit.

10. The microfluidic cartridge of claim 9, wherein the reagent chamber stores a reagent selected from a wash buffer, an enzyme substrate, a dilution buffer, a conjugate, an enzyme-labeled conjugate, a DNA amplifier, a sample diluent, a wash solution, a detergent, a polymer, a chelating agent, an albumin-binding reagent, an enzyme inhibitor, an enzyme, an anticoagulant, a red-cell agglutinating agent, and an antibody.

11. The microfluidic cartridge of claim 1, wherein the microfluidic cartridge comprises all reagents necessary to perform the assay to detect the analyte.

12. The microfluidic cartridge of claim 1, wherein the microfluidic cartridge comprises a length of about 7 cm to about 30 cm, and a width of about 5 cm to about 30 cm.

13. The microfluidic cartridge of claim 1, further comprising a plurality of reactant chambers of a plurality of assay units, and wherein each reactant chamber of the plurality of reactant chambers comprises a reaction site with a different reactant immobilized on the reaction site for reacting with a different analyte in the bodily fluid sample.

14. A point-of-care system for detecting an analyte in a bodily fluid sample, comprising:
a microfluidic cartridge, comprising:
a sample collection unit comprising a sample collection well for receiving the bodily fluid sample,
an assay unit in fluid communication with the sample collection well, wherein the assay unit comprises a reactant chamber having a reaction site with a reactant immobilized on the reaction site and configured to react with the analyte in the bodily fluid sample to generate a colored product having an absorbance spectrum, and
a light source comprising a luminescent paint coated on the reaction site, wherein a spectrum of light emitted from the luminescent paint has at least one wavelength that is a function of the absorbance spectrum; and
a bench-top reader assembly configured to receive the microfluidic cartridge, wherein the bench-top reader assembly comprises:
one or more actuating elements that direct and control a flow of the bodily fluid sample from the sample collection unit to the assay unit of the microfluidic cartridge, and
a detector configured to detect an absorption of light of the at least one wavelength, wherein the absorption of light is indicative of the presence of the analyte.

15. The point-of-care system of claim 14, wherein the reader assembly further comprises a controller configured to control the one or more actuating elements according to a protocol for conducting the assay to detect the analyte.

16. The point-of-care system of claim 15, wherein the reader assembly further comprises a communication assembly for transmitting a signal detected by the detector to an external device for processing.

17. The point-of-care system of claim 14, wherein the detector is an optical detector.

18. The point-of-care system of claim 14, wherein the microfluidic cartridge further comprises a waste chamber in fluid communication with the reactant chamber, and wherein the reader assembly is further configured to direct flow of the bodily fluid sample from the reactant chamber to the waste chamber.

19. The point-of-care system of claim 14, wherein the microfluidic cartridge further comprises a reagent chamber that stores a reagent for conducting the assay to detect the analyte, and
wherein the reader assembly is configured to direct flow of the reagent from the reagent chamber to the reactant chamber.

* * * * *